United States Patent
Lapkowicz et al.

(10) Patent No.: US 11,557,861 B2
(45) Date of Patent: *Jan. 17, 2023

(54) HERMETICALLY SEATED CONTROLLED IMPEDANCE FEEDTHROUGH ASSEMBLY

(71) Applicant: Ardent Concepts, Inc., Hampton, NH (US)

(72) Inventors: Victor A Lapkowicz, Durham, NH (US); Gordon A Vinther, Hampton, NH (US)

(73) Assignee: Ardent Concepts, Inc., Hampton, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/645,477

(22) Filed: Dec. 22, 2021

(65) Prior Publication Data

US 2022/0115819 A1    Apr. 14, 2022

Related U.S. Application Data

(63) Continuation of application No. 16/948,419, filed on Sep. 17, 2020, now Pat. No. 11,223,167.

(60) Provisional application No. 62/901,297, filed on Sep. 17, 2019.

(51) Int. Cl.
| | |
|---|---|
| *H01R 12/00* | (2006.01) |
| *H01R 13/6586* | (2011.01) |
| *H01R 13/52* | (2006.01) |
| *H01R 13/6597* | (2011.01) |
| *H01R 24/44* | (2011.01) |

(52) U.S. Cl.
CPC ....... *H01R 13/6586* (2013.01); *H01R 13/521* (2013.01); *H01R 13/6597* (2013.01); *H01R 24/44* (2013.01)

(58) Field of Classification Search
CPC ..................... H01R 23/7073; H01R 13/5208
See application file for complete search history.

(56) References Cited

U.S. PATENT DOCUMENTS

| | | | |
|---|---|---|---|
| 5,735,697 A | 4/1998 | Muzslay | |
| 7,740,488 B2 * | 6/2010 | Taylor | H01R 12/91 439/66 |
| 8,926,342 B2 | 1/2015 | Vinther et al. | |
| 10,439,317 B2 * | 10/2019 | Horchler | H01R 12/79 |
| 11,223,167 B2 * | 1/2022 | Lapkowicz | A61N 1/3754 |
| 2008/0140148 A1 | 6/2008 | Rogier | |
| 2009/0079517 A1 | 3/2009 | Iyer | |

(Continued)

OTHER PUBLICATIONS

Written Opinion for PCT Application No. PCT/US2020/070547, dated Mar. 15, 2021.

(Continued)

*Primary Examiner* — Phuong Chi Thi Nguyen

(57) ABSTRACT

An assembly for passing controlled impedance electrical signals between two different environments via feedthroughs in an electrically-conductive feedthrough block. The feedthrough has a signal coupling, a dielectric spacer surrounding the signal coupling, and a ground coupling surrounding the dielectric. The feedthrough is sealed to hermetically separate the two environments. One or both ends of the dielectric are recessed from the face of the block forming a gap. The gaps is filled with a potting material to form the hermetic seal.

14 Claims, 26 Drawing Sheets

(56) References Cited

U.S. PATENT DOCUMENTS

2014/0262493 A1 9/2014 Markham et al.
2015/0165220 A1 6/2015 Markham et al.

OTHER PUBLICATIONS

International Search Report for PCT Application No. PCT/US2020/070547, dated Mar. 15, 2021.
Office Action for U.S. Appl. No. 16/948,419 dated Feb. 24, 2021.

* cited by examiner

HERMETICALLY SEATED CONTROLLED IMPEDANCE FEEDTHROUGH ASSEMBLY

The present application is a continuation of U.S. patent application Ser. No. 16/948,419 which claims the benefit of U.S. Provisional Patent Application No. 62/901,297, both of which are hereby incorporated by reference in their entireties.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to electrical cable feedthrough assemblies, more particularly, to controlled-impedance cable feedthroughs which are generally used to transmit high-frequency signals between different physical environments.

2. Description of the Related Art

In some scenarios, signals must be fed between different environments. Examples include between environments with different atmosphere gasses, environments of different atmospheric pressures, and environments of different levels of sterility. In such cases, the interface must be hermetically sealed so that the environments do not intermix or so that one environment does not contaminate the other.

In the current state of the art, individual coaxial connectors, such as SMAs or SMPs, are used to transmit signals between environments. These connectors are fairly large, 0.25 inch to 0.5 inch in diameter. Since they cannot be any closer to each other than their largest diameter, the number of connectors per unit area separating the environments, the density, is rather low.

BRIEF SUMMARY OF THE INVENTION

The present specification describes an assembly for passing signals between two different environments. The signals, which are typically RF, are passed through a first connector in the first environment, through feedthroughs in a flange that separates the two environments, and through a second connector in the second environment. Each connector terminates one or more controlled-impedance cables.

The connectors has several embodiments, representative ones of which have an anchor block for securing the cables, compliant signal contacts for making electrical connections between the cable signal conductors and the feedthroughs, optional compliant ground contacts for making electrical connections between the cable shields and the feedthroughs, and a plate mounted to the anchor block 88 that holds the contacts.

An electrically conductive anchor block provides a common ground for the cables that are either permanently or removably attached to the anchor block. Alternatively, the anchor block is non-conductive and merely provides an anchor for the cables that are removably attached.

The connector can be designed for use with any number of different compliant contacts. A plate holds the contacts and can be composed of an electrically conductive or electrically insulative material. The plate abuts the anchor block face when the connector is assembled and generally abuts the feedthrough block when the connector is connected to the feedthrough block. The signal contact is captured in a through aperture in the plate. If the plate is conductive, the signal contact is insulated from the plate. Prior to assembling the plate to the anchor block, the contact points of the signal contact extend from each side of the plate. Each ground contact is captured in a ground through aperture. Prior to assembling the plate to the anchor block, the contact points of the ground contact extend from each side of the plate.

The signals travel through the flange via feedthroughs in a feedthrough block. The feedthrough has three components: a signal coupling, a dielectric surrounding the signal coupling, and a ground coupling surrounding the dielectric. If the block is electrically insulating, the block itself can act as the dielectric. If the block is electrically conductive, a separate dielectric is required.

A feedthrough without a separate dielectric has a signal through aperture in the block for a signal link, which is an electrically conductive wire or pin. The ends of the signal link are the contact points for the signal contacts of the connectors. Optionally, the signal link and signal aperture are shaped to prevent the signal link from being pushed through the signal aperture during installation or if the first environment is at a higher pressure than the second environment.

A feedthrough with a separate dielectric has a spacer through aperture in the block with the dielectric in the form of a dielectric spacer. Optionally, the spacer aperture and spacer are shaped to prevent the spacer from being pushed through the spacer aperture during installation or if the first environment is at a higher pressure than the second environment. The spacer has a signal through aperture for the signal link.

Typically, the aperture, spacer, and signal link are sized to provide impedance matching for the signals using methods that are well-known in the art. For an accurate impedance match, the dielectric must be surrounded by the system ground plane. If the block is electrically conductive, no special accommodation for the ground signal is needed. A non-conductive block must feed the ground signal through the block by a ground coupling.

The ground coupling can include discrete electrically conductive ground links that extend through ground apertures in the block. The appropriate number of ground links surround the signal link. The ground links are electrically conductive wires or pins. Alternatively, the ground links are plated vias. In another configuration, the ground coupling is an electrically conductive ground ferrule installed in a ground ferrule through aperture in the block that surrounds the spacer. In another configuration, the wall of the spacer aperture is coated with a conductive material.

The various components are installed with a hermetic seal to hermetically separate the two environments. In one method, the various components are press fit into the corresponding apertures, leaving no gap between adjacent components. Alternatively, the spacer is molded around the signal link and press fit into the spacer through aperture.

In another method, the spacer is shorter than the spacer aperture so that one or both faces of the spacer are recessed from the corresponding block surface, thereby leaving a gap between the spacer and the block surface. One or both of the gaps are potted to seal the spacer aperture and around the signal link, thereby producing a hermetic seal. The typical potting material is a two-part epoxy. The minimum depth for each gap depends on the environment and the potting material and is typically not less than 0.01 inch. Plated vias are hermetically sealed by filling them with the potting material or solder.

One method of potting involves applying a vacuum to one surface of the block and allowing the vacuum to pull the potting material from the opposite side, thereby forcing the potting material into the gap and all of the interfaces between components. The vacuum assures that the potting material is forced into all of the spaces that would provide a leak path. Alternatively, pressure is applied to the potting material at one surface to push the potting material into all of the spaces that would provide a leak path.

The present invention contemplates that the flange is the block, that is, the feedthroughs extend through the flange itself. Alternatively, the block is an independent component that is hermetically sealed into an opening in the flange.

Objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
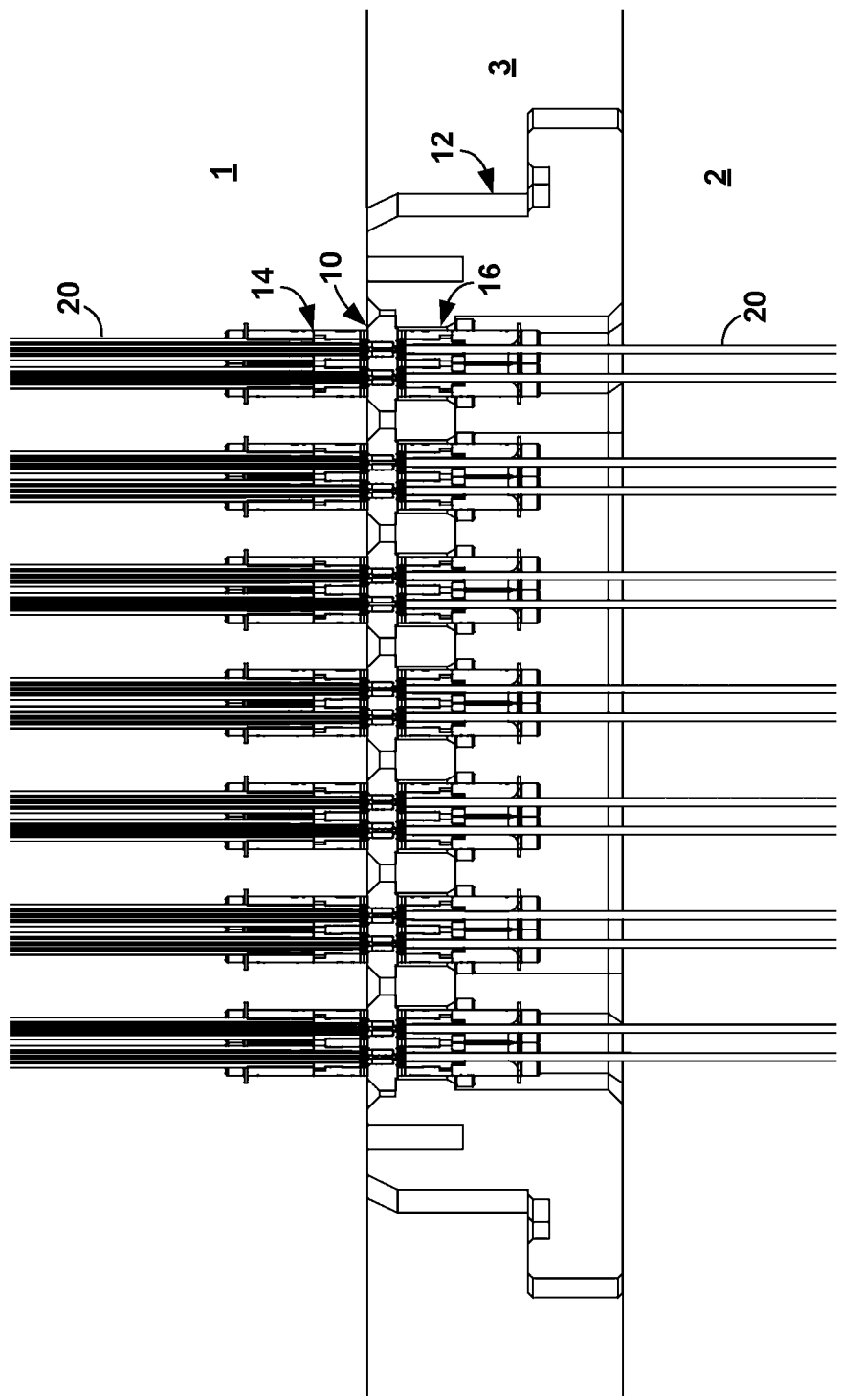
FIG. 1 is a cross-section of one embodiment.

The present specification describes an assembly 10 for passing signals between a first environment 1 and a second environment 2 separated by a barrier 3. The two environments 1, 2 can be different in many respects. For example, there can be pressure, temperature, or chemical compounds on either side of the barrier 3 which are not to be mixed in some applications. An example of such a situation is feeding data into and out of a cold computing environment, such as a quantum computing environment. The first environment 1 is typically at normal atmospheric pressure and room temperature. In a quantum computing environment, the second environment 2 is at a near perfect vacuum. The region of the second environment 2 closest to the first environment 1 is near room temperature and the temperature of the region farthest from the first environment 1 is kept between 4 Kelvin and 4 milliKelvin.

Figure 2:
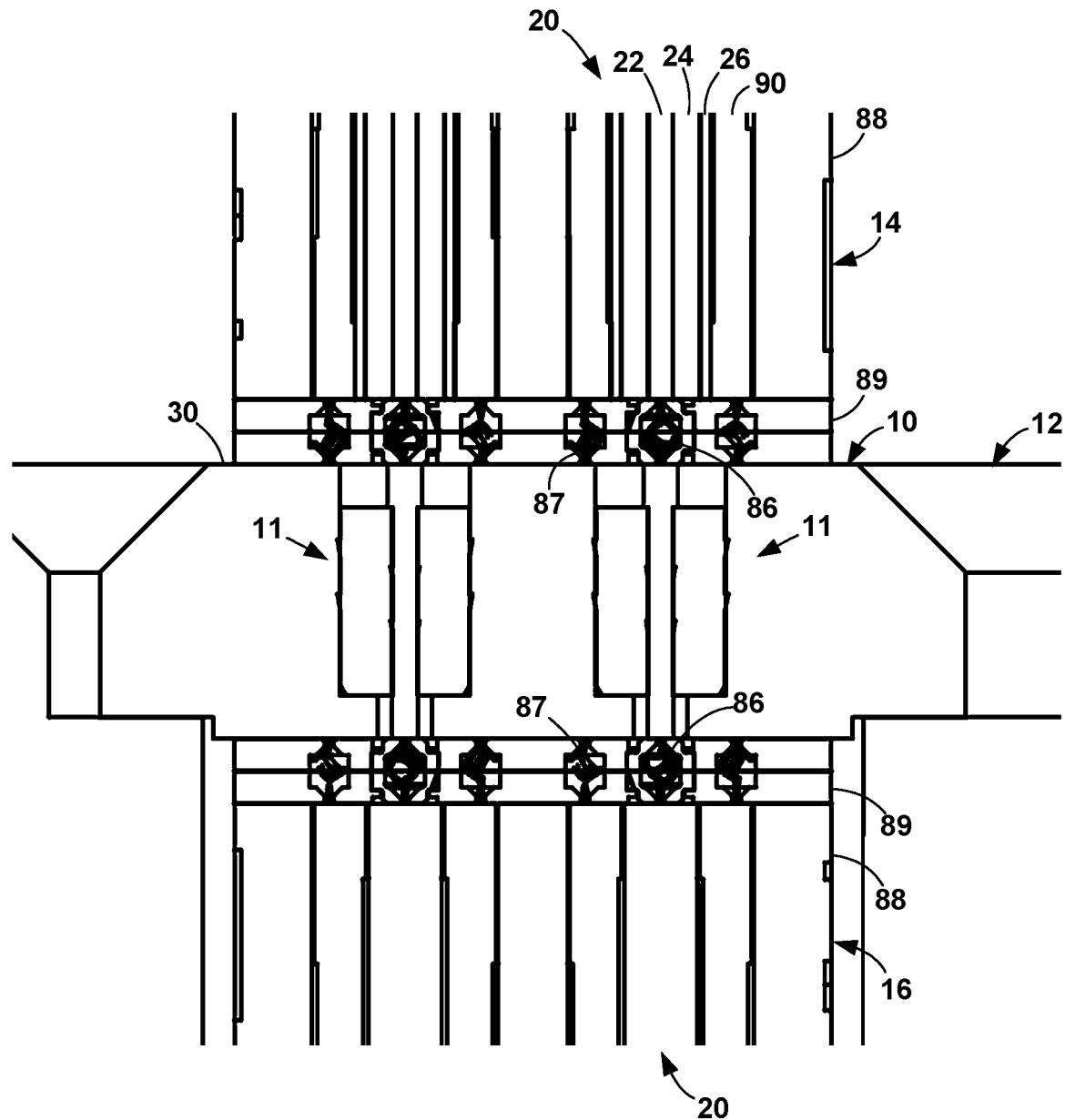
FIG. 2 is a detail of FIG. 1.

As shown in FIGS. 1 and 2, the signals are passed between the environments 1, 2 through a first connector 14 in the first environment 1, a flange 12 that separates the two environments 1, 2, and a second connector 16 in the second environment 2. The signals are typically radio frequency, RF, signals. Signal speeds can be as low as a few hundred MHz to as high as 70 GHz depending on the application, though the upper end of the frequency range with which the present invention can be employed is constantly being improved upon.

Each connector 14, 16 terminates one or more controlled-impedance cables 20. A controlled-impedance coaxial cable 20 has a signal conductor 22 surrounded by a dielectric 24 with a ground reference shield 26 outside the dielectric 24. Optionally, a sheath 28 covers the shield 26. A controlled-impedance twin-axial cable 20 has two signal conductors 22 surrounded by a dielectric 24 with a ground reference shield 26 outside the dielectric 24 and a sheath 28 covering the shield 26. In order for the cable 20 to be terminated properly, the cable ground shield 26 must be electrically coupled to the connector 14,16. Optionally, a ferrule 90 can be installed on the ground shield 26, as in FIG. 2. Controlled-impedance cables 20 with more than two signal conductors 22 are available. Although not specifically described, the present invention can be adapted to accommodate cables 20 having any number of signal conductors 22.

The flange 12 removably mounts into an opening in the barrier 3 that separates the two environments 1, 2. The flange 12 is mounted in any manner that provides an acceptable hermetic seal between the flange 12 and the barrier 3. Methods of mounting are well-known in the industry. Alternatively, the barrier 3 incorporates the flange 12, that is, the barrier 3 and flange 12 are not separate components.

The signals travel through the flange 12 via feedthroughs 11 in a feedthrough block 30. The connectors 14, 16 provide the interface between the controlled-impedance coaxial cables (hereinafter, simply "cable") 20 and the feedthroughs 11. Different configurations of the connectors 14, 16 are described in U.S. Pat. Nos. 8,926,342 and 9,160,151, both of which are incorporated herein by reference. Several of the configurations are summarized below. Only one connector 14 is referenced hereinafter.

The connector 14 has several embodiments, representative ones of which have an anchor block 88 for securing the cables 20, compliant signal contacts 86 for making electrical connections between the cable signal conductors 22 and the feedthroughs 11, optional compliant ground contacts 87 for making electrical connections between the cable shields 26 and the feedthroughs 11, and a plate 89 mounted to the anchor block 88 that holds the contacts 86, 87.

Figure 3:
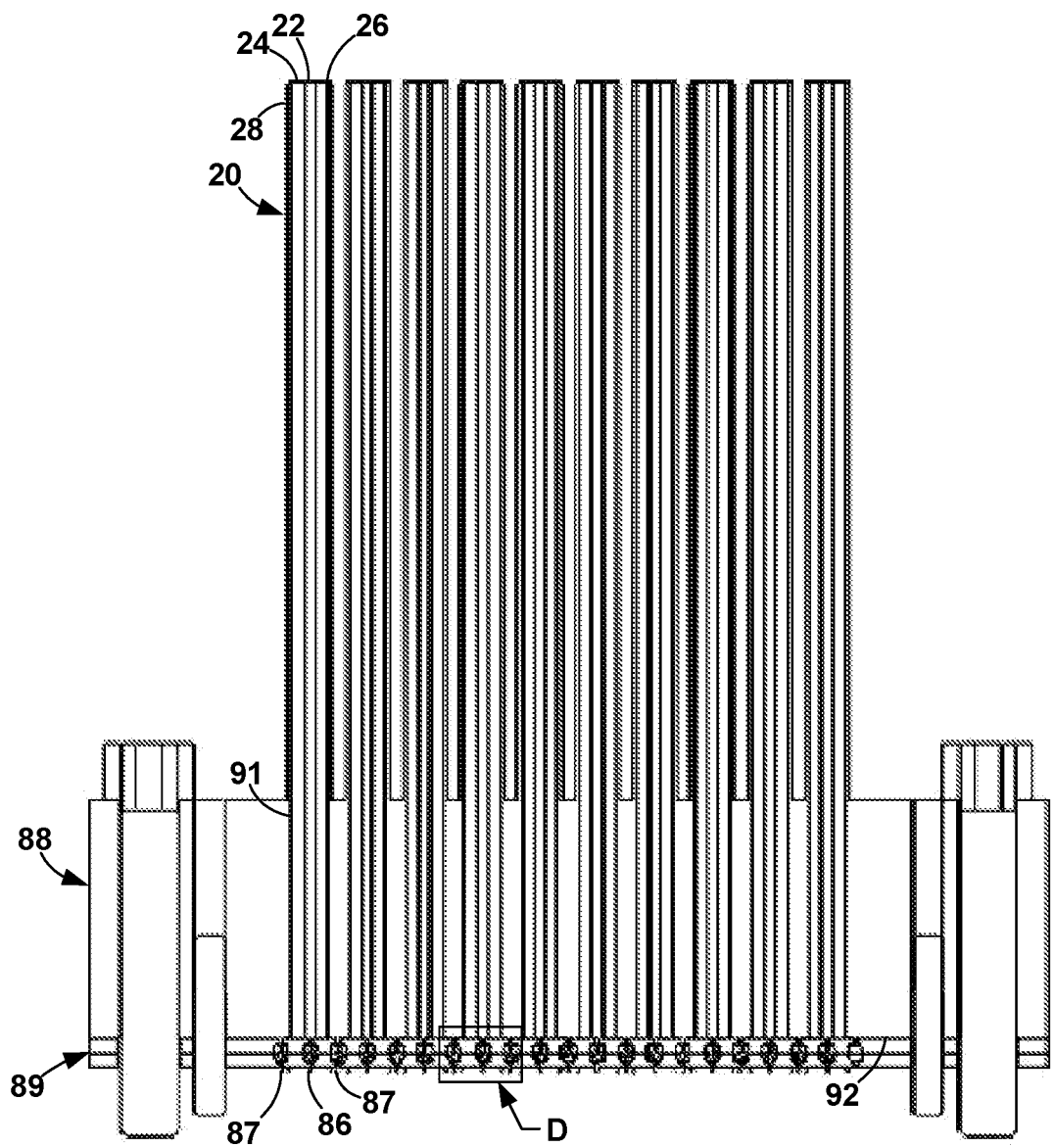
FIG. 3 is a cross-sectional view of a section of a configuration of the connector of FIG. 1 with permanently attached cables.

In one configuration, the anchor block 88 is electrically conductive and provides a common ground for the cables 20 that are permanently attached, as in FIG. 3. The ground shields 26 of all of the cables 20 are electrically connected to the anchor block 88 in holes 91 in the anchor block 88. Any adequate method can be used, including soldering, crimping, potting with a conductive adhesive, insert molding the anchor block 88 with the cable 20 in place at the time of molding, and press fitting a rigidized, for example, pretinned, ground shield 26 into the hole 91.

Once the cables 20 are anchored in the anchor block 88, the face 92 of the anchor block 88, the signal conductors 22, and the dielectrics 24 are properly dressed to make reliable electrical contacts with the compliant contacts 86, 87. The anchor block face 92, signal conductor 22, and dielectric 24 may need to be polished and planarized by some mechanical means, such as by milling, grinding, or sanding, in order to make sure that the cable center conductors 22 and dielectrics 24 are positioned at a known depth with respect to the anchor block face 92, in this case flush with the anchor block face 92. The anchor block face 92 and signal conductors 22 may also require noble metal plating to prevent the polished surface from oxidizing or otherwise degrading so as to inhibit acceptable electrical connection of the contacts 86, 87 to the signal conductors 22 and the anchor block 88.

Figure 4:
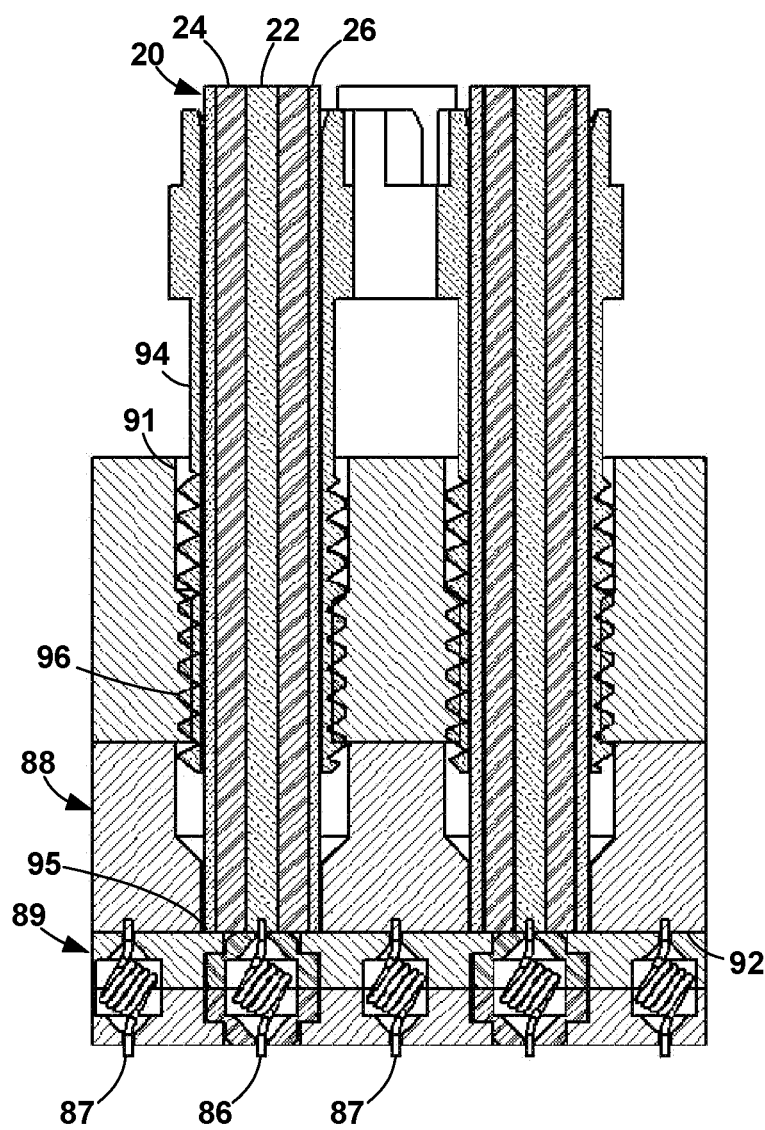
FIG. 4 is a cross-sectional view of a section of a configuration of the connector with removable cables.
Figure 5:
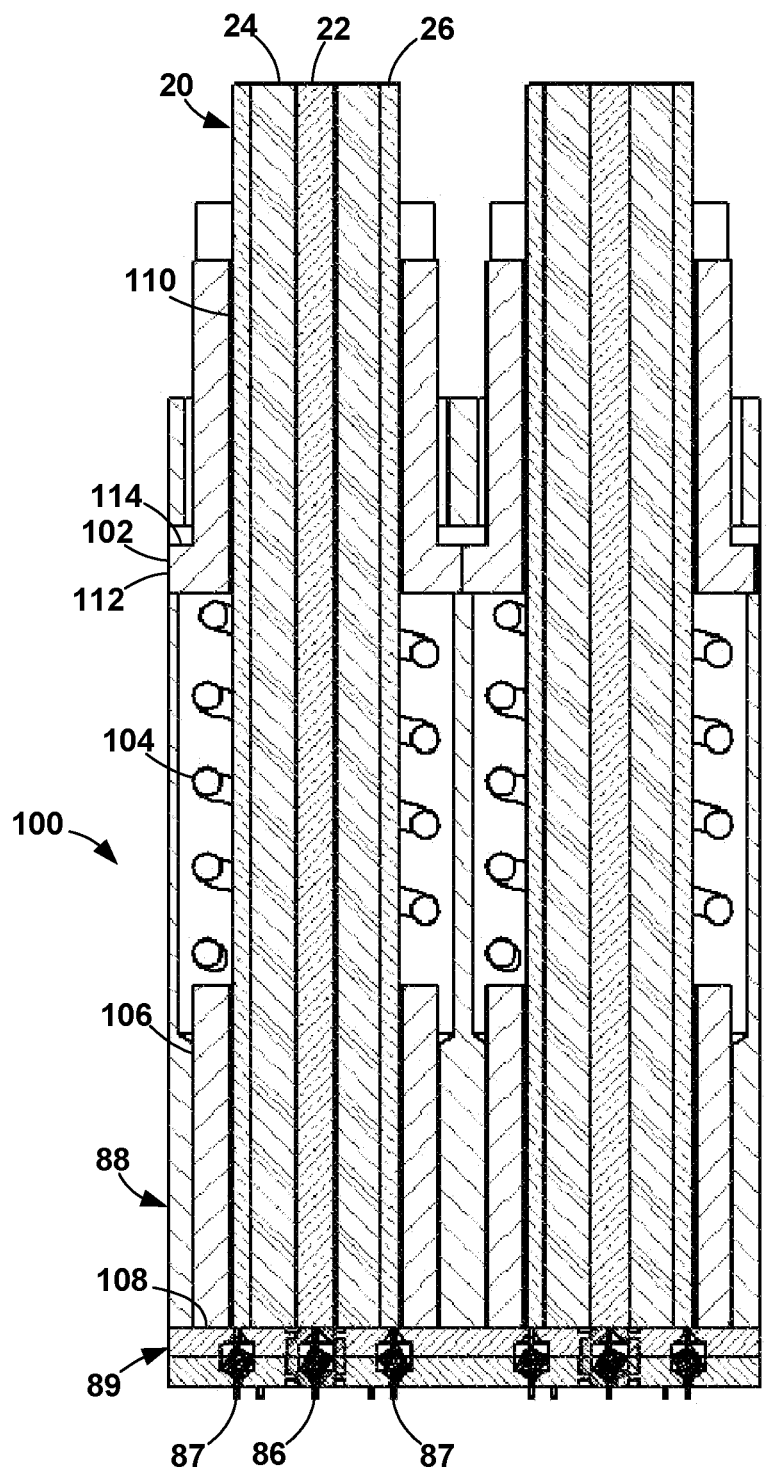
FIG. 5 is a cross-sectional view of a section of another configuration of the connector with removable cables.
Figure 6:
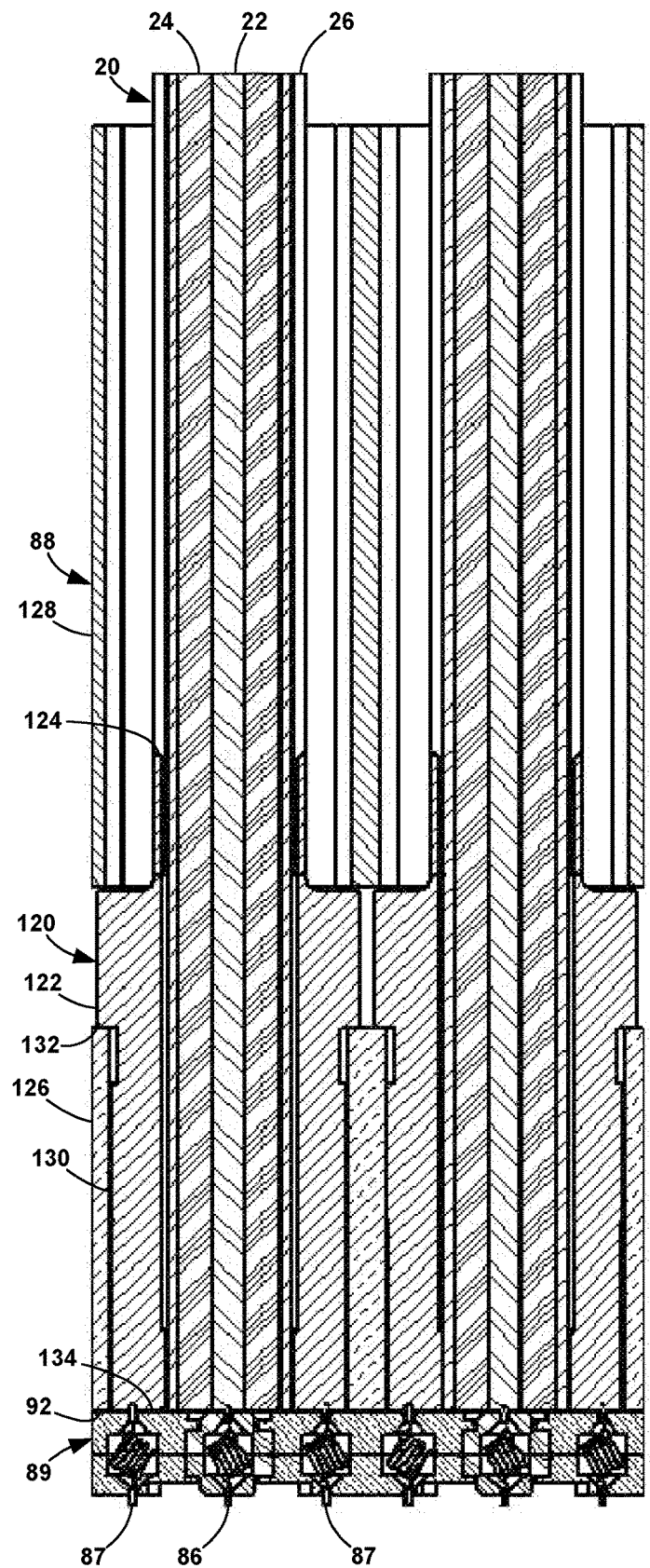
FIG. 6 is a cross-sectional view of a section of another configuration of the connector with removable cables.

In another configuration, the anchor block 88 is either conductive or nonconductive and merely provides an anchor for the cables 20 that are removably attached. Methods of removably attaching the cable 20 to the anchor block 88 are shown in FIGS. 4-6. These methods permit replacement of individual cables 20 so the entire assembly does not have to be replaced.

The first method, shown in FIG. 4, calls for attaching a ferrule at or near the end of the cable 20 for dressing the cable end. The sheath 28 is stripped back and a threaded ferrule 94 is slipped over the shield 26. The ferrule 94 is attached to the cable 20 by soldering, crimping, or other mechanical means that electrically couples the ferrule 94 to the shield 26. The ferrule face 95, signal conductor 22, and dielectric 24 are then dressed as described above with reference to the anchor block 88. The ferrule 94 is threaded into a threaded hole 96 in the anchor block 88 until the signal conductor 22 is pressed against the signal contact 86 in order to produce an electrical connection between the signal conductor 22 and the signal contact 86.

The second method of removably attaching the cable 20 to the anchor block 88 calls for the use of a twist-lock attachment 100, as shown in FIG. 5. A twist-lock component 102 is slipped over the cable 20 such that the component 102 can slide freely over the cable 20. A coil spring 104 is slipped over the cable 20. After the sheath 28 is stripped back, a ferrule 106 is attached to the shield 26 by soldering, crimping, or other mechanical means that electrically couples the ferrule 106 to the shield 26. The ferrule face 108, signal conductor 22, and dielectric 24 are then dressed as described above with reference to the anchor block 88.

The ferrule 106/cable 20 is inserted into a hole 110 in the anchor block 88. Protrusions 112 from the twist-lock component 102 slide down opposed notches, not shown, in the sides of the hole 110 until they align with an annular depression 114 in the hole 110. With this alignment, the spring 104 is compressed so that it presses the signal conductor 22 to the signal contact 86 in order to produce an electrical connection between the signal conductor 22 and the signal contact 86. The twist-lock component 102 is turned so that the protrusions 112 are captured by the annular depression 114, thereby retaining the cable 20 in the hole 110.

Another method of removably attaching the cable 20 to the anchor block 88 is shown in FIG. 6. A ferrule 120 is attached to the cable 20 and dressed as described above. The ferrule 120 has an annular ridge 122 either at the end 124 of the ferrule 120 or away from the end 124, as in FIG. 6. The anchor block 88 has two sections, a bottom section 126, and a top section 128. The upper end of the cable hole 130 in the bottom section 126 has an annular groove 132. When the ferrule 120/cable 20 assembly is inserted into the cable hole 130, the ridge 122 fits into the groove 132 with the ferrule face 134, signal conductor 22, and dielectric 24 flush with the block face 92. The block top section 128 is installed on the bottom section 126 and attached via screws, clips, or any other acceptable method. The top section 126 captures the ferrule 120/cable 20 assembly in the anchor block 88. Optionally, the ridge 122 and groove 132 can be keyed to prevent the ferrule 120/cable 20 assembly from rotating in the cable hole 130.

In some situations, particularly with removable attachments, the signal conductor 22 and/or dielectric 24 may not be exactly flush with the anchor block face 92, that is, it may be slightly recessed into or protruding from the anchor block face 92. That recession or protrusion can be as much as 0.05 inch. The present specification and claims use the term, "flush", to indicate that the signal conductor 22 and dielectric 24 are actually flush with, slightly recessed into, or slightly protruding from the anchor block face 92 by as much as 0.05 inch.

The connector 14 can be designed for use with any number of different compliant contacts, including, but not limited to, skewed coil contacts, fuzz button contacts, conductive rubber contacts, and conductive strip contacts. FIGS. 3-8 show the connector as designed for use with skewed coil contacts. Skewed coil contacts of various types and configurations are described in U.S. Pat. Nos. 7,126,062 and Re41,663, both of which are incorporated herein by reference. Briefly, the skewed coil contact includes a coil of conductive, inherently elastic wire with a pair of oppositely extending leads. The leads extend in a direction angled from the coil axis. During compression, the coil loops are electrically shorted together while they slide along each other.

Figure 7:
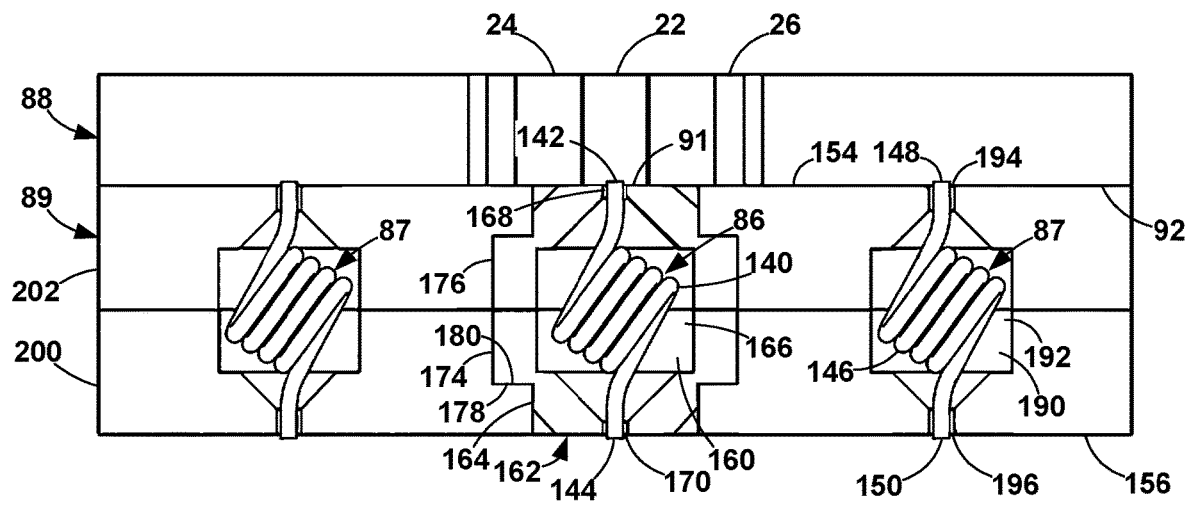
FIG. 7 is a cross-sectional view of one configuration of the plate with a portion of the anchor block and cable.
Figure 8:
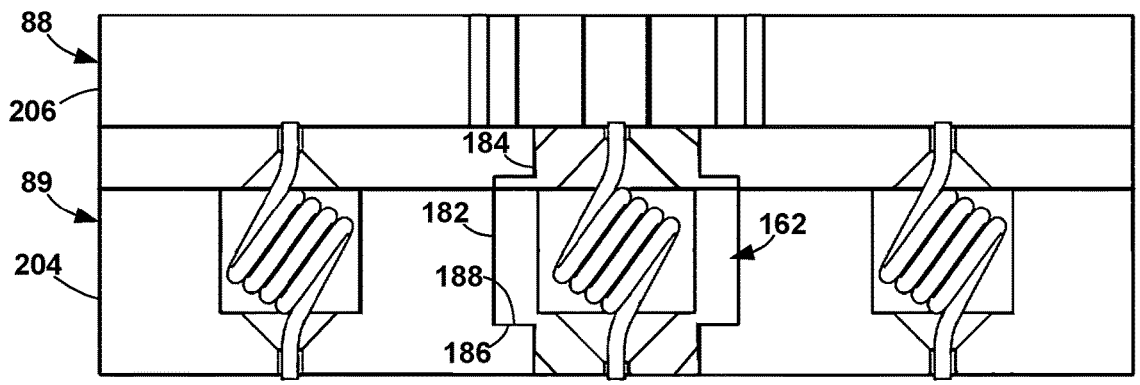
FIG. 8 is a cross-sectional view of another configuration of the plate with a portion of the anchor block and cable.

The plate 89, shown in FIGS. 7 and 8, holds the contacts 86, 87 and can be composed of an electrically conductive or electrically insulative material.

The plate 89 has a block surface 154 that abuts the anchor block face 92 when the connector 14 is assembled and a feedthrough surface 156 that generally abuts the feedthrough block 30 when the connector 14 is connected to the feedthrough block 30. Typically, the plate 89 is attached to the anchor block face 92 by screws 216.

As shown in FIG. 7, the signal contact 86 is captured in a through aperture 160 in the plate 89. The signal through aperture 160 has a larger center section 166 that narrows to a smaller signal block opening 168 in the block surface 154 and to a smaller signal feedthrough opening 170 in the feedthrough surface 156. The coil 140 of the contact 86 is captured in the center section 166. Prior to assembling the plate 89 to the anchor block 88, the block contact point 142 of the signal contact 86 extends from the signal block opening 168. Prior to connecting the connector 14 to the feedthrough block 30, the feedthrough contact point 144 of the signal contact 86 extends from the signal feedthrough opening 170.

If the plate 89 is conductive, the signal through aperture 160 is within an insulating plug 162 that prevents the signal contact 86 from electrically shorting to the plate 89. The plug 162 is typically made from an insulating plastic. The plug 162 fits in a signal through hole 164 in the plate 89.

After the plate 89 is assembled to the anchor block 88, each signal block opening 168 is aligned with its corresponding cable hole 91 in the anchor block 88.

Each ground contact 87 is captured in a ground through aperture 190. Each ground through aperture 190 has a larger center section 192 that narrows to a smaller ground block opening 194 in the block surface 154 and to a smaller ground feedthrough opening 196 in the feedthrough surface 156. The coil 146 of the ground contact 87 is captured in the center section 192. Prior to assembling the plate 89 to the anchor block 88, the block contact point 148 of the ground contact 87 extends from the ground block opening 194. Prior to connecting the connector 14 to the feedthrough block 30, the feedthrough contact point 150 of the ground contact 87 extends from the ground feedthrough opening 196.

When composed of a conductive material, the plate 89 electrically couples the ground contacts 87, thus providing more precise impedance matching to the signal contact 86.

In the configuration of FIG. 7, the plate 89 has two mirror image sheets 200, 202. The bottom sheet 200 has the feedthrough openings 170, 196 and half of the center sections 166, 192, and the top sheet 202 has the block openings 168, 194 and half of the center sections 166, 192. The contacts 86, 87 are placed in the center section 166, 192 of one sheet 200 and the sheets 200, 202 are sandwiched together to capture the contacts 86, 87.

In the configuration of FIG. 8, the plate 89 has a bottom sheet 204 with the feedthrough openings 170, 196 and the entirety of the center sections 166, 192, and a top sheet 206 with only the block openings 168. The contacts 86, 87 are placed in the center section 166, 192 of the bottom sheet 204 and the sheets 204, 206 are sandwiched together to capture the contacts 86, 87.

When an insulating plug 162 is used, it may be press fit into the through hole 164 in the plate 89 or it may be bonded into the through hole 164 with an adhesive. Alternatively, as shown in FIG. 7, the plug 162 has two parts 174, 176, each of which fit into one plate sheet 200, 202. Mating shoulders 178, 180 retain the plug parts 174, 176 in the plate sheets 200, 202. Alternatively, as shown in FIG. 8, the plug 162 is has a lower part 182 and an upper part 184, which fit into the lower sheet 204 and upper sheet 206, respectively. Mating shoulders 186, 188 retain the plug parts 182, 184 in the plate sheets 204, 206.

Figure 9:
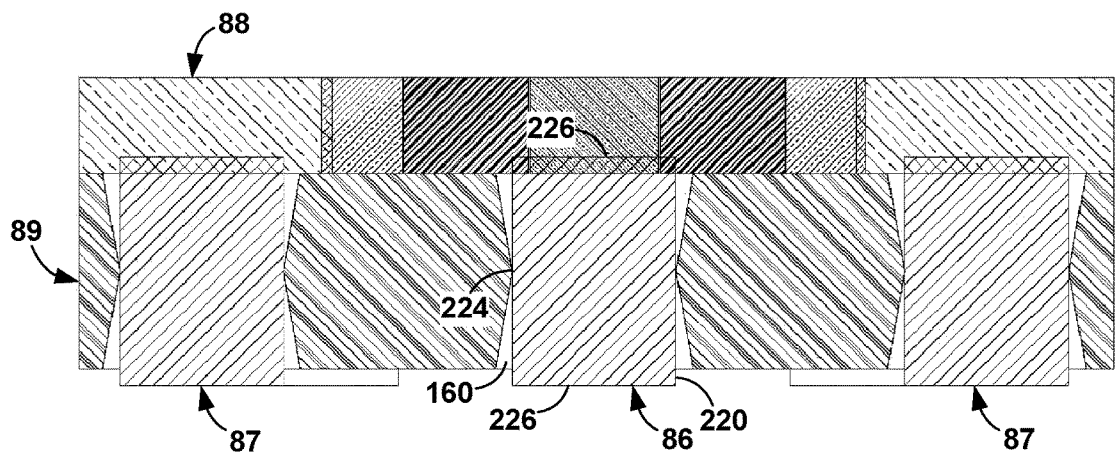
FIG. 9 is a cross-sectional view of an insulative plate with fuzz button contacts.

As mentioned above, fuzz button contacts can be employed. As shown in FIG. 9, the fuzz button contact 220 is cylindrical. The plate 89 has a through aperture 160 that is narrower at the center than the ends, as at 224. The contact 220 is forced into the aperture 160. The length of the contact 220 is such that the ends 226 extend from the plate 89.

Figure 10:
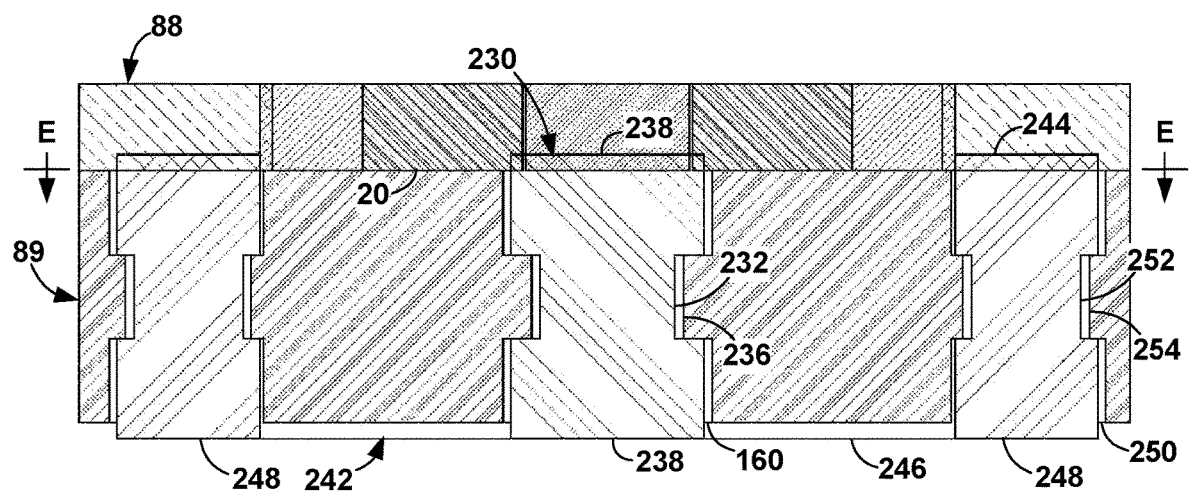
FIG. 10 is a cross-sectional view of an insulative plate with conductive rubber contacts.
Figure 11:
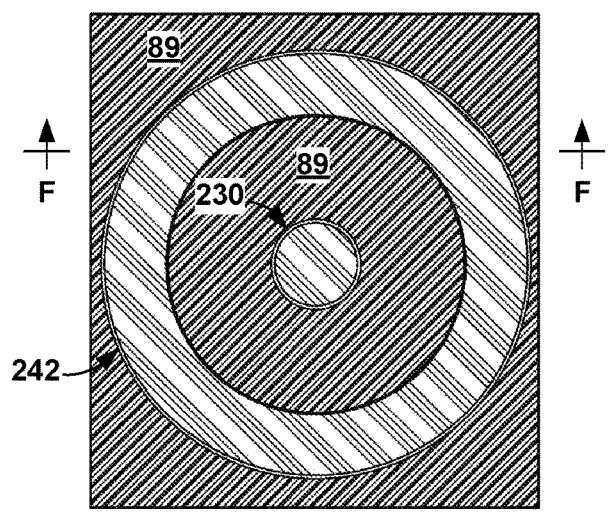
FIG. 11 is a cross-sectional view taken at E-E of FIG. 10.
Figure 12:
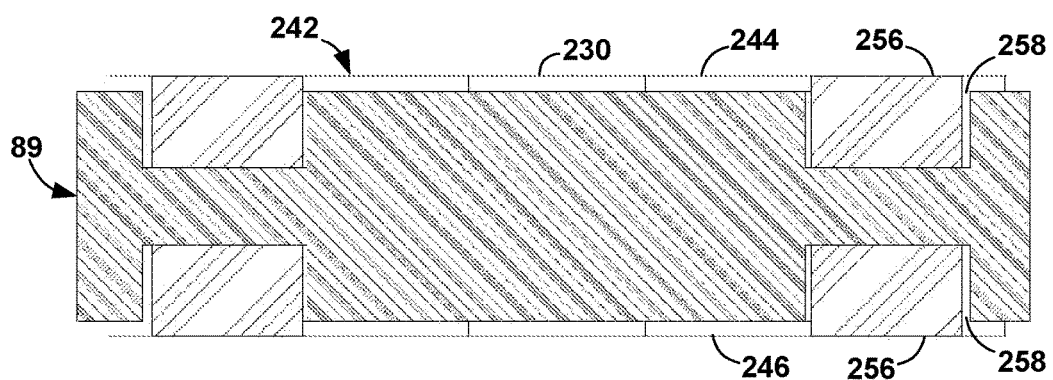
FIG. 12 is a cross-sectional view taken at F-F of FIG. 11.
Figure 13:
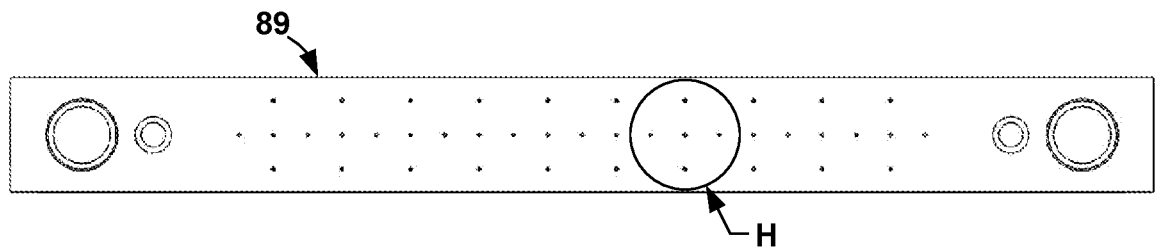
FIG. 13 is bottom view of an insulative plate with embedded stamped or etched contacts.
Figure 14:
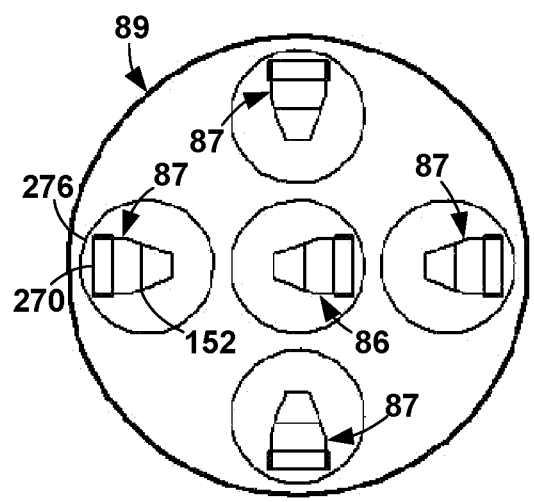
FIG. 14 is a detail view of the bottom of the coax cable termination assembly of FIG. 13 taken at H.
Figure 15:
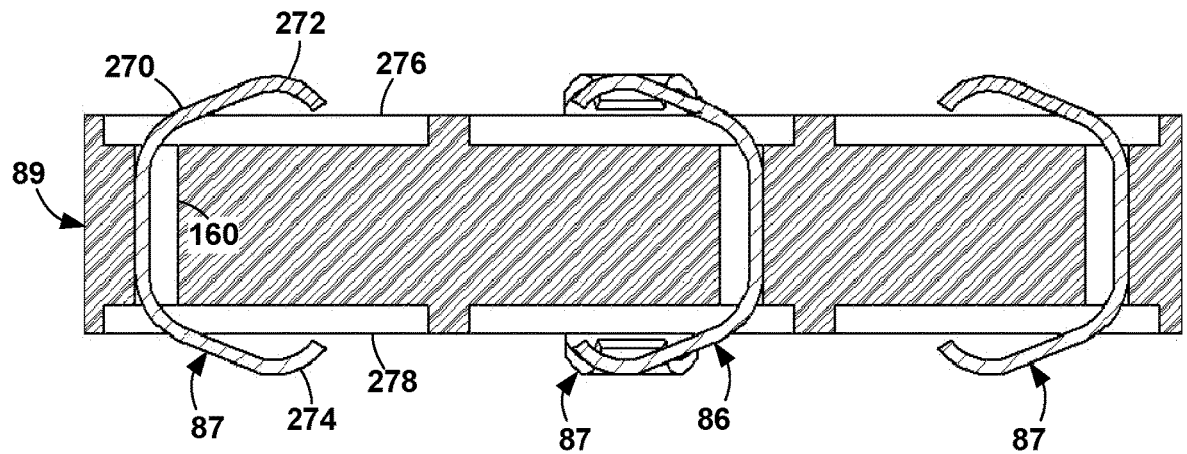
FIG. 15 is a cross-sectional view of the plate of FIG. 13.
Figure 16:
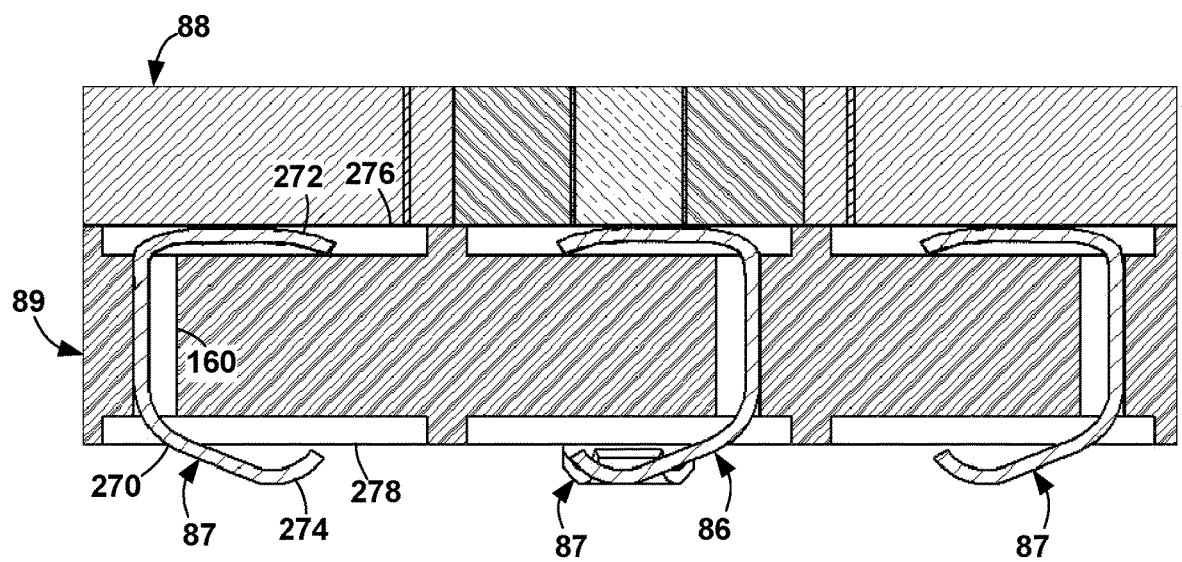
FIG. 16 is a cross-sectional view of an insulative plate with embedded stamped or etched contacts with one side mated to the cables and the contacts compressed.
Figure 17:
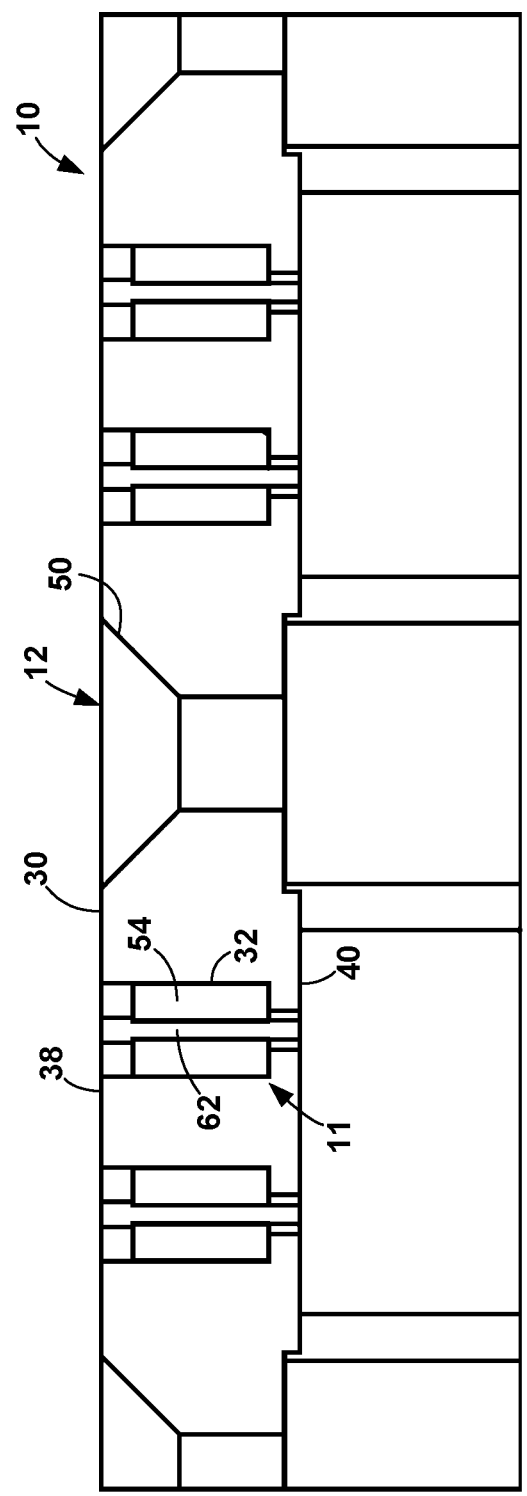
FIG. 17 is a cross-section of a block separate from the flange.

As mentioned above, conductive rubber contacts can be employed. As shown in FIGS. 10-12, the conductive rubber contact 230 for the signal contact 86 can be cylindrical with a centrally located annular depression 232. The plate 89 has a through aperture 160 with a centrally located annular protrusion 236. The conductive rubber contact 230 is radially compressed and placed in the aperture 160 such that the protrusion 236 fits into the depression 232 to retain the contact 230 in the aperture 160. The length of the contact 230 is such that the ends 238 extend from the plate 89.

The conductive rubber contact for the ground contact 87 can be of the same structure as the signal contact 86. Alternatively, the conductive rubber contact 242 for the ground contact 87 is circular, surrounding the signal contact 86, as in FIG. 11. The conductive rubber contact 242 has a circular top sheet 244 adjacent to the anchor block 88 and a circular bottom sheet 246 for interfacing to the feedthrough block 30. The two sheets 244, 246 are electrically connected by a plurality of plugs 248 in through apertures 250 in the plate 89. The number of plugs 248 can vary by application and is typically four or eight spaced evenly around the signal contact 230. As with the signal contact 230, each plug 248 has an annular depression 252 that fits into an annular protrusion 254 for retention. Knobs 256 extending from the sheets 244, 246 into depressions 258 in the plate 89, as in FIG. 12, to help retain the sheets 244, 246 in position.

As mentioned above, conductive strip contacts can be employed. In FIGS. 13-16, the contact 270 is a strip of conductive material in a C shape. The contact can be formed by chemical etching, by stamping and forming, or by any other means practical. The contact 270 is captured in a through aperture 160 in the plate 89. In their quiescent state, the contact leads 272 extend outwardly of the plate 89, as in FIG. 15. When the anchor block 88 is attached to the plate 89, the upper lead 272 deforms toward the plate 89 and into a depression 276, shown in FIG. 16, thereby providing electrical contact by the signal contact 86 to the signal conductor 22 and by the ground contacts 87 to the anchor block 88. When the assembly is connected to the feedthrough block 30, the lower lead 274 deforms toward the plate 89 and into a depression 278.

As indicated above, the signals travel through the flange 12 via feedthroughs 11 in a feedthrough block 30, shown in FIGS. 1, 2, 17, and 34. The first surface 38 of the block 30 is designed to tolerate the first environment 1 and the second surface 40 of the block 30 is designed to tolerate the second environment 2.

The feedthrough block 30 has a feedthrough 11 for each signal that passes between the two environments 1, 2 through the flange 12. In order to accurately pass a controlled impedance signal, the feedthrough 11 requires at least three components: a signal coupling 61, a dielectric 53 surrounding the signal coupling 61, and a ground coupling 70 surrounding the dielectric 53.

The feedthrough 11 has two different configurations that differ based on the materials of which the block 30 is composed. If the block 30 is composed of an electrically insulating material, the block 30 itself can act as the dielectric 53. If the block 30 is composed of an electrically conductive material, a separate dielectric 53 is required.

Figure 18:
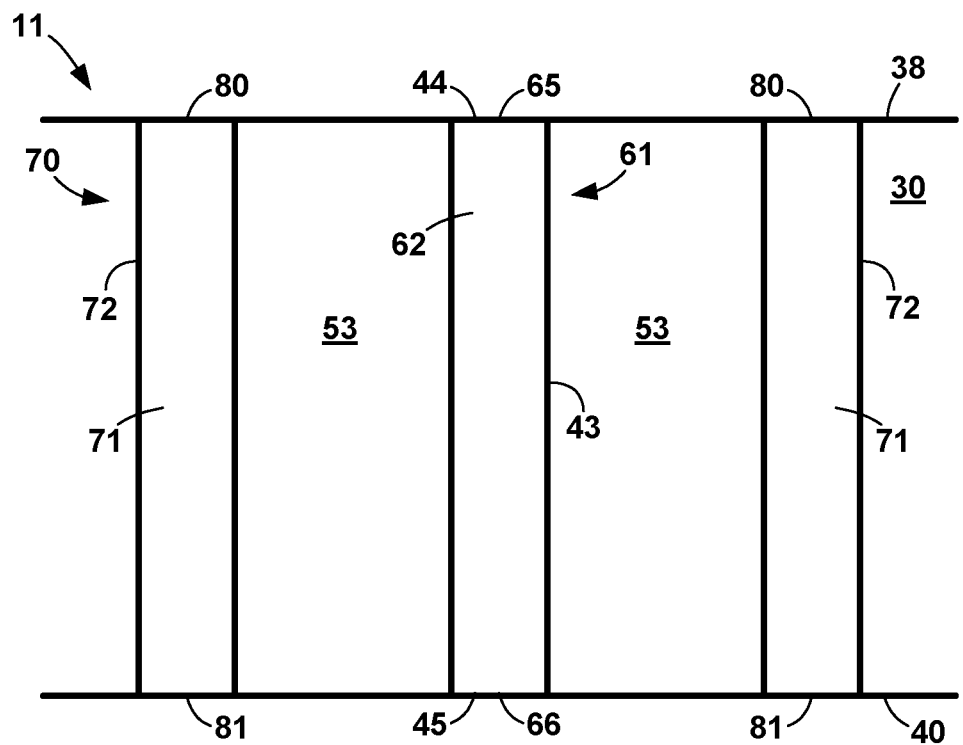
FIG. 18 is a cross-section of a basic feedthrough without a separate dielectric.
Figure 19:
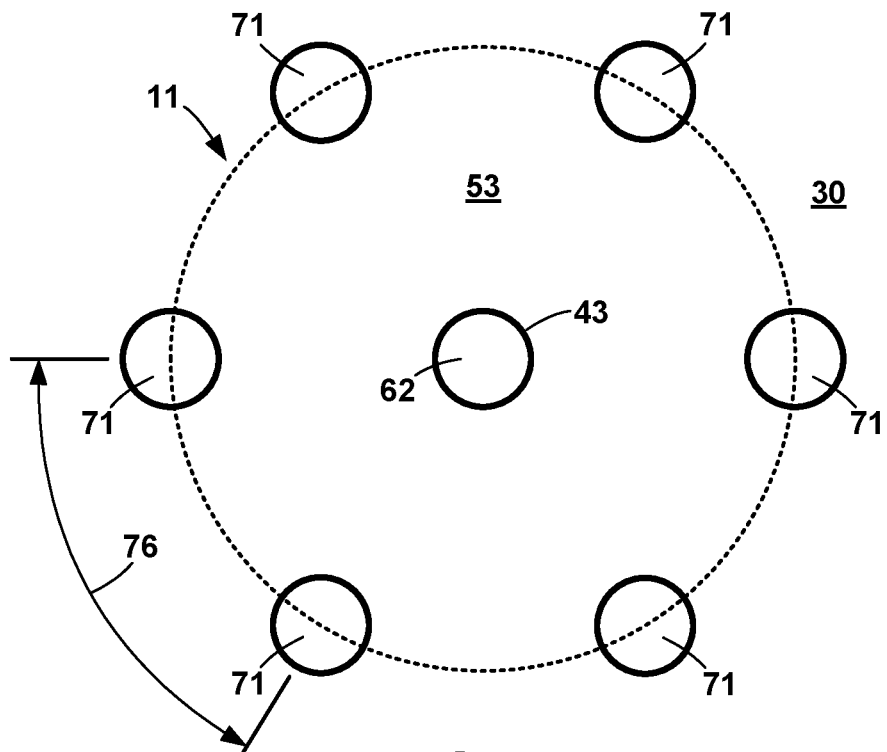
FIG. 19 is a top view of the feedthrough of FIG. 18.

A feedthrough 11 without a separate dielectric is shown in FIGS. 18 and 19. The feedthrough 11 has a signal through aperture 43 in the block 30 that extends between a first opening 44 in a first surface 38 of the block 30 and a second opening 45 in a second surface 40 of the block 30. As shown in FIG. 19, the signal through aperture 43 is typically round, but can be other shapes.

The signal coupling 61 includes a signal link 62 that extends through each signal aperture 43. The signal link 62 is an electrically conductive wire or pin and can be composed of any electrically conductive material adequate to the application. Typically, the signal link 62 will be composed of a copper alloy. In one configuration, the signal link 62 is composed of beryllium copper plated with gold over nickel. If a nonmagnetic signal link 62 is desired, gold plated beryllium copper can be used. The signal link 62 can also be composed of non-electrically conductive materials as long as the signal link 62 can conduct electricity. For example, the signal link 62 can be composed of a non-electrically conductive plastic or composite that is embedded or coated with electrically conductive materials that render the signal link 62 electrically conductive.

The signal link 62 has a first end 65 at the block first surface 38 and a second end 66 at the block second surface 40. The signal link ends 65, 66 are the contact points for the signal contacts 86 of the connectors 14, 16. Optionally, the signal ends 65, 66 are flush with the corresponding block surface 38, 40. Due to inaccuracies and tolerances in the manufacturing process, the signal link ends 65, 66 may not be exactly flush with the corresponding block surface 38, 40, that is, they may be slightly recessed into or protruding from the corresponding block surface 38, 40. Typically, the recession is not more than 0.0005 inch and the protrusion is not more than 0.001 inch, but can be as much as 0.05 inch. If the protrusion or recession is greater than allowable, the affected signal link end 65, 66 and the corresponding block surface 38, 40 can be polished and planarized by some mechanical means, such as by milling, grinding, or sanding, in order to make sure that the signal link end 65, 66 is at a known depth with respect to the block surface 38, 40, in this case flush with the ground block face 20. The polished ends 65, 66 may also require noble metal plating to prevent them from oxidizing or otherwise degrading so as to inhibit acceptable electrical connections.

The present specification and claims use the term, "flush", to indicate that the signal link ends 65, 66 are actually flush with, slightly recessed into, or slightly protruding from the corresponding block surface 38, 40 by as much as 0.05 inch.

The signal link 62 has a cross-sectional shape that allows a proper fit, mechanically and electrically, in the signal aperture 43. In the figures, the signal aperture 43 and signal link 62 are both round. However, as long as the junction is structurally sound, the signal aperture 43 and the signal link 62 can be different cross-sectional shapes. For example, the signal aperture 43 can be round and the signal link 62 can be octagonal.

Optionally, the signal link 62 and signal aperture 43 are shaped to prevent the signal link 62 from being pushed through the signal aperture 43 during installation or if the first environment 1 is at a higher pressure than the second environment 2. In general, the diameter of the signal link first end 65 is larger than a diameter of signal aperture 43. In one configuration, shown in FIG. 20, the signal link first end 65 has a head 63 that has a larger diameter than the rest of the signal link 62 and the signal aperture 43. In another configuration, shown in FIG. 21, the signal link 62 is a truncated cone rather than cylindrical. The signal aperture 43 is shaped to match such that, when the signal link 62 is securely within the signal aperture 43, each end 65, 66 is at the corresponding block surface 38, 40. Any other geometries that prevent the signal link 62 from being pushed through the signal aperture 43 are contemplated by the present invention.

The ground coupling 70 is discussed below.

As indicated above, if the block 30 is composed of an electrically conductive material, a separate dielectric 53 is required, as shown in FIGS. 22-25. A separate dielectric 53 can also be used if the block 30 is composed of an electrically insulating material that does not have the necessary dielectric characteristics.

Figure 23:
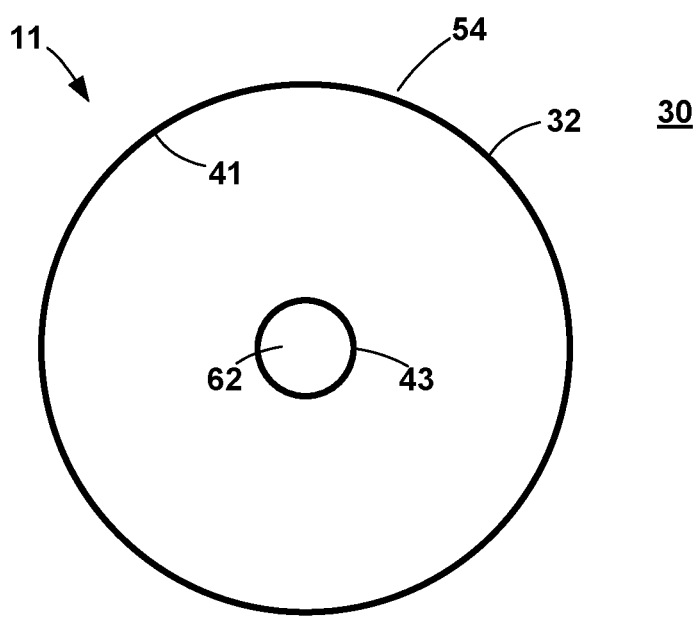
FIG. 23 is a top view of the feedthrough of FIG. 22.
Figure 25:
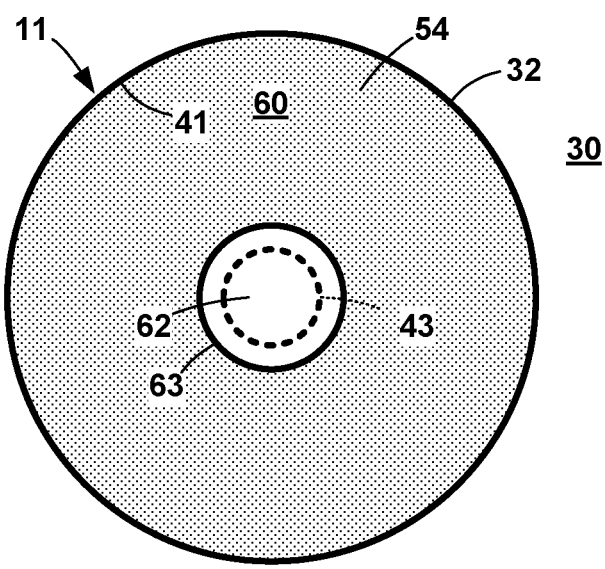
FIG. 25 is a top view of the feedthrough of FIG. 24.

The feedthrough 11 has a spacer through aperture 32 in the block 30 that extends between a first opening 34 in a first surface 38 of the block 30 and a second opening 36 in a second surface 40 of the block 30. As shown in FIGS. 23 and 25, the spacer through aperture 32 is typically cylindrical but can be other shapes.

Within the spacer through aperture 32 is the dielectric 53 in the form of a dielectric spacer 54. The spacer 54 has a cross-sectional shape that allows a proper fit, mechanically and electrically, in the spacer aperture 32. In the figures, the spacer aperture 32 and spacer 54 are both round. However, as long as the spacer 54 has the proper impedance and is structurally sound, the spacer aperture 32 and the spacer 54 can be different cross-sectional shapes. For example, the spacer aperture 32 can be round and the spacer 54 can be octagonal.

Optionally, the spacer aperture 32 and spacer 54 are shaped to prevent the spacer 54 from being pushed through the spacer aperture 32 during installation or if the first environment 1 is at a higher pressure than the second environment 2. In general, the first face 54 of the spacer 54 is larger than the second opening 36 of the spacer aperture 32. In one configuration, shown in FIG. 24, the spacer aperture 32 has a stepped diameter, as at 48, to provide a shoulder 49. The spacer 54 abuts the shoulder 49 to prevent the spacer 54 from falling or being pushed through the spacer aperture 32. In another configuration, the spacer 54 is a truncated cone rather than cylindrical, similar to the signal link 62 of FIG. 21. The spacer aperture 32 is shaped to match such that, when the spacer 54 is securely within the spacer aperture 32, each end 56, 57 located appropriately relative to the corresponding block surface 38, 40. Any other geometries that prevent the spacer 54 from being pushed through the spacer aperture 32 are contemplated by the present invention.

The material from which the spacer 54 is made is chosen depending on the application. The dielectric constant of the spacer 54 has a value necessary to produce a desired impedance environment, usually 50 ohms, although other impedances maybe desired. The dielectric constant can range from 1.1-15 but usually around 3-4. Typically, the spacer 54 is an engineered plastic (polyetheretherketone, PEEK) that is picked for its dielectric constant (Dk) value and resulting signal integrity performance. In one configuration, Dk is 3.3, chosen so that the impedance of the feedthrough is 50 ohms. Different Dk values can be used depending on the desired impedance, the diameter of the aperture 32, and the diameter of the signal link 62.

The spacer 54 has one or more signal through apertures 43 that extend between a first opening 44 in the first face 56 and a second opening 45 in the second face 57 of the spacer 54. For a coaxial cable 20, there is a single signal aperture 43 that is axially aligned in the spacer 54. For a cable 20 with more than one signal conductor 22, the spacer 54 has a signal aperture 43 for each signal conductor 22 and the signal apertures 43 are aligned paraxially and arranged for impedance matching, as described below.

The signal link 62 extends through each signal aperture 43. As described above, the signal link 62 is an electrically conductive wire or pin.

As described above, the signal link 62 has a first end 65 at the block first surface 38 and a second end 66 at the block second surface 40. Optionally, the signal ends 65, 66 are flush with the corresponding block surface 38, 40.

As described above, the signal link 62 is typically round, and can be shaped to prevent the signal link 62 from being pushed through the signal aperture 43 during installation or if the first environment 1 is at a higher pressure than the second environment 2.

The remainder of the present specification is illustrated by the configuration with the spacer 54. It is understood that the following descriptions also apply to the configuration without the spacer 54 with the appropriate modification.

Optionally, the aperture 32, spacer 54, and signal link 62 are sized to provide impedance matching for the signals. Methods for doing so are well-known in the art, including equations and software simulators, such as HFSS (high-frequency structure simulator). The key parameters include the materials, Dk values, and dimensions.

In order for the feedthrough to provide an accurate impedance match, the dielectric 53 must be surrounded by the system ground plane. If the block 30 is electrically conductive, no special accommodation for the ground signal is needed. The block 30 itself is the contact point for the ground contacts 87 of the connectors 14, 16.

A non-conductive block 30 must feed the ground signal between surfaces 38, 40 by a ground coupling 70. This can be accomplished in a number of different ways.

Figure 28:
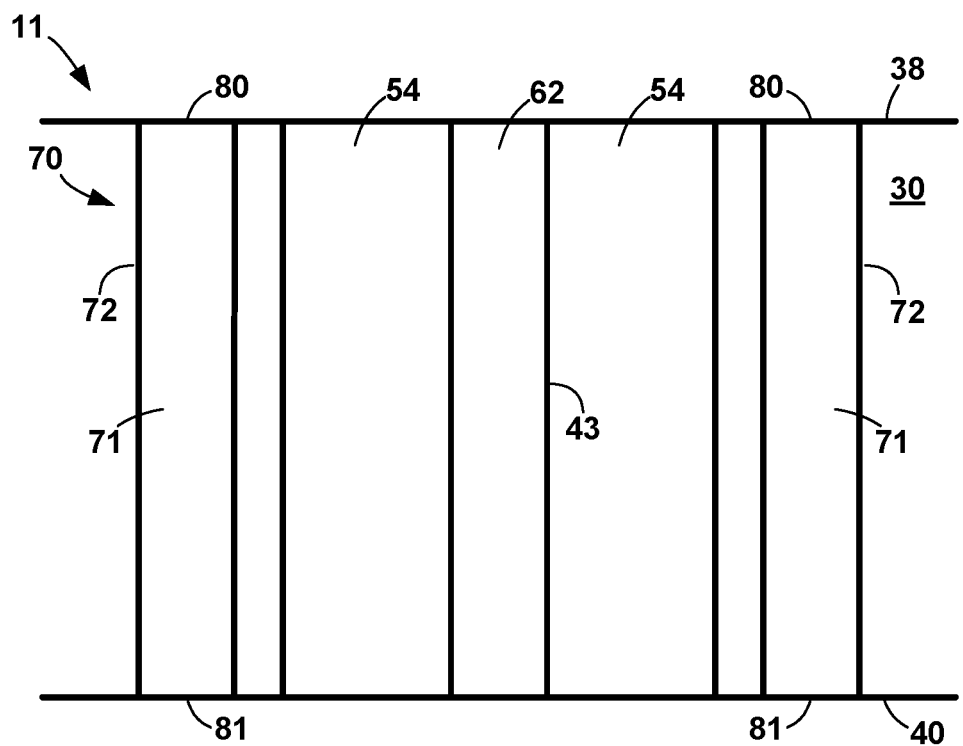
FIG. 28 is a cross-sectional view of a feedthrough with ground links.
Figure 29:
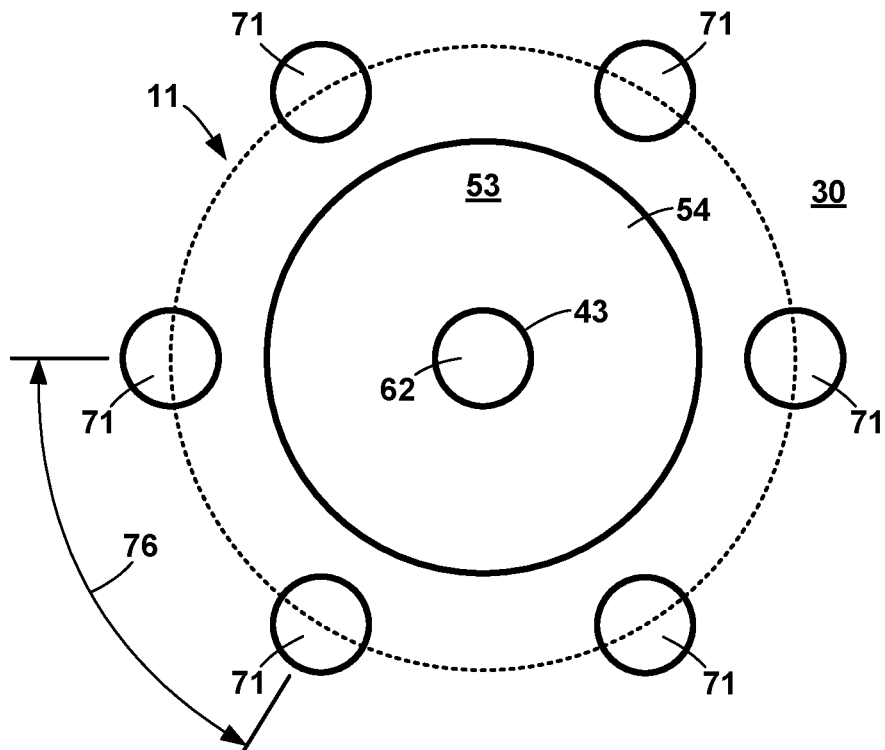
FIG. 29 is a top view of a feedthrough with ground links surrounding the signal link and spacer.

In one configuration, the ground coupling 70 can include discrete electrically conductive ground links 71 that extend through ground apertures 72 in the block 30, as in FIGS. 18 and 28. The ground links 71 surround the signal link 62, as in FIGS. 19 and 29, so that the ground signal surrounds the spacer 54/signal link 62. The specific number of ground links 71 used to surround the signal link 62 and their distances from the signal link 62 will be determined by the parameters of the particular application, such as the desired impedance environment, the diameters of the signal link 62 and spacer 54, and the materials of which the block 30 and spacer 54 are composed. The ground links 71 will typically be arranged equidistantly around a circle the surrounds the aperture 32. For example, if there are six ground links 71, they will be 60° apart, as at 76 in FIGS. 19 and 29.

The ground links 71 are electrically conductive wires or pins and can be composed of any electrically conductive material adequate to the application. Typically, the ground links 71 will be composed of a copper alloy. In one configuration, the ground links 71 are composed of beryllium copper plated with gold over nickel. If nonmagnetic ground links 71 are desired, gold plated beryllium copper can be used. The ground links 71 can also be composed of non-electrically conductive materials as long as the ground links 71 can conduct electricity. For example, the ground links 71 can be composed of a non-electrically conductive plastic or composite that is embedded or coated with electrically conductive materials that render the ground links 71 electrically conductive.

Figure 20:
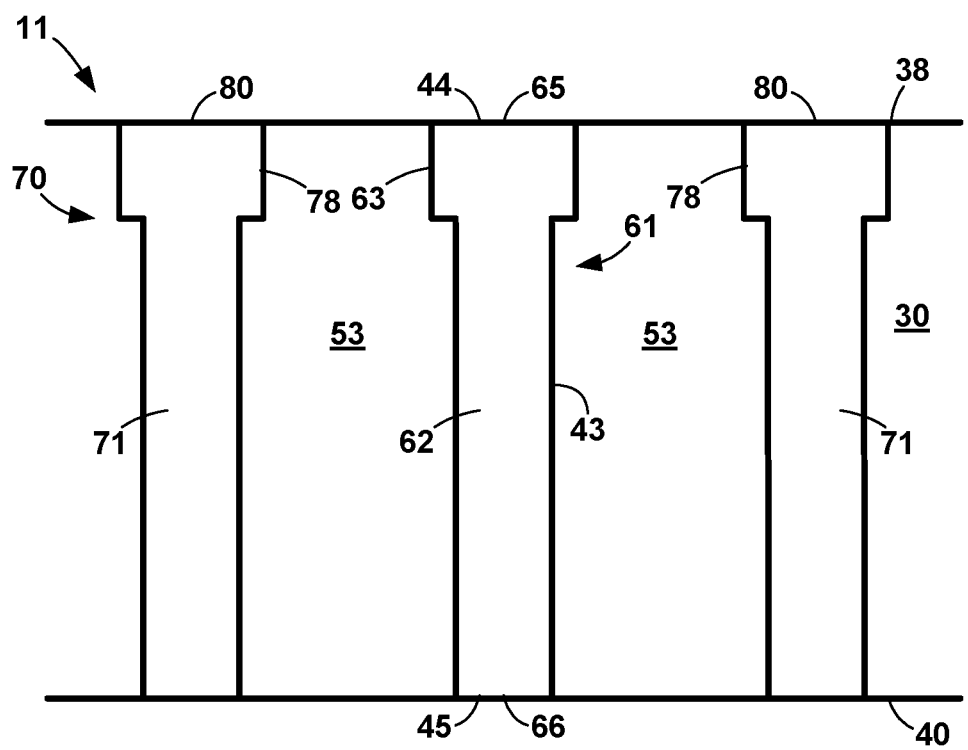
FIG. 20 is a cross-section of a feedthrough with an alternate configuration of the signal link and signal aperture.
Figure 21:
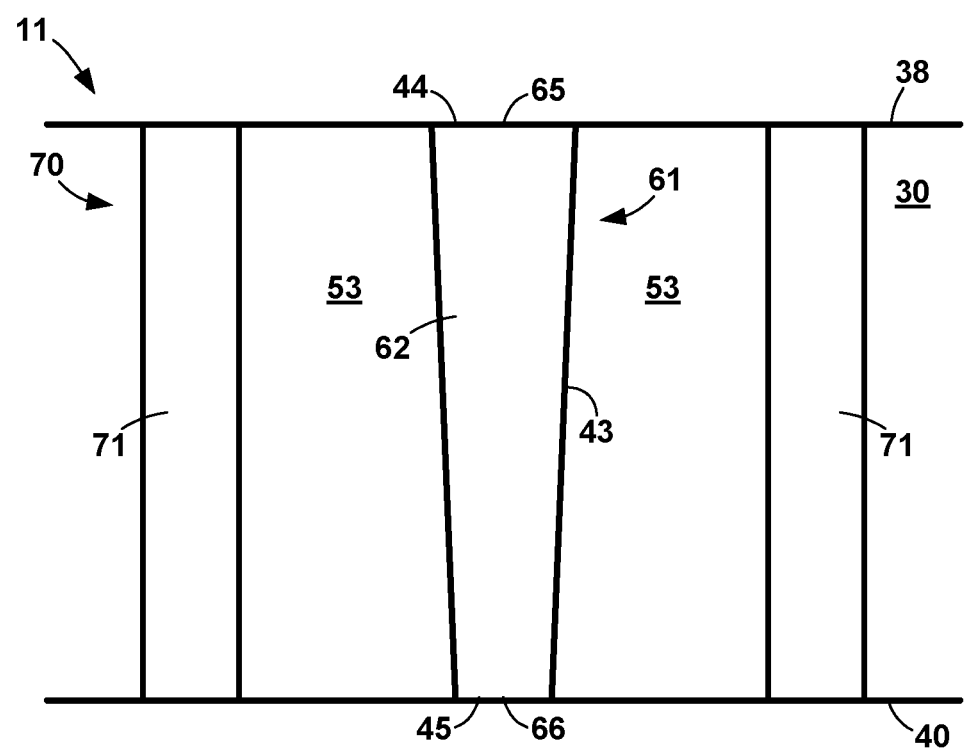
FIG. 21 is a cross-section of a feedthrough with an alternate configuration of the signal link and signal aperture.
Figure 22:
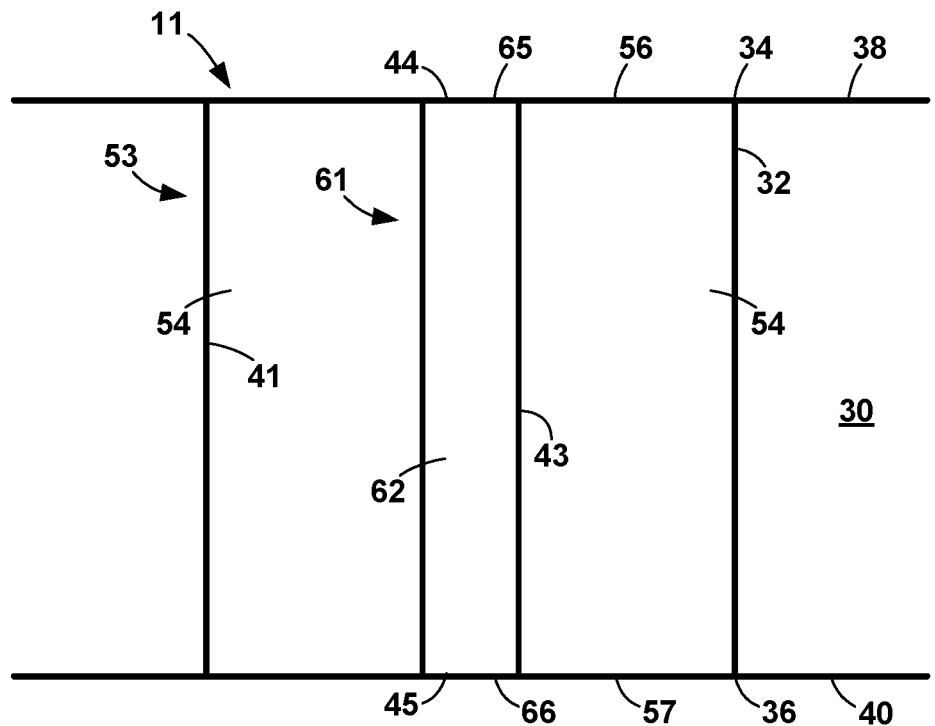
FIG. 22 is a cross-section of a basic feedthrough.
Figure 30:
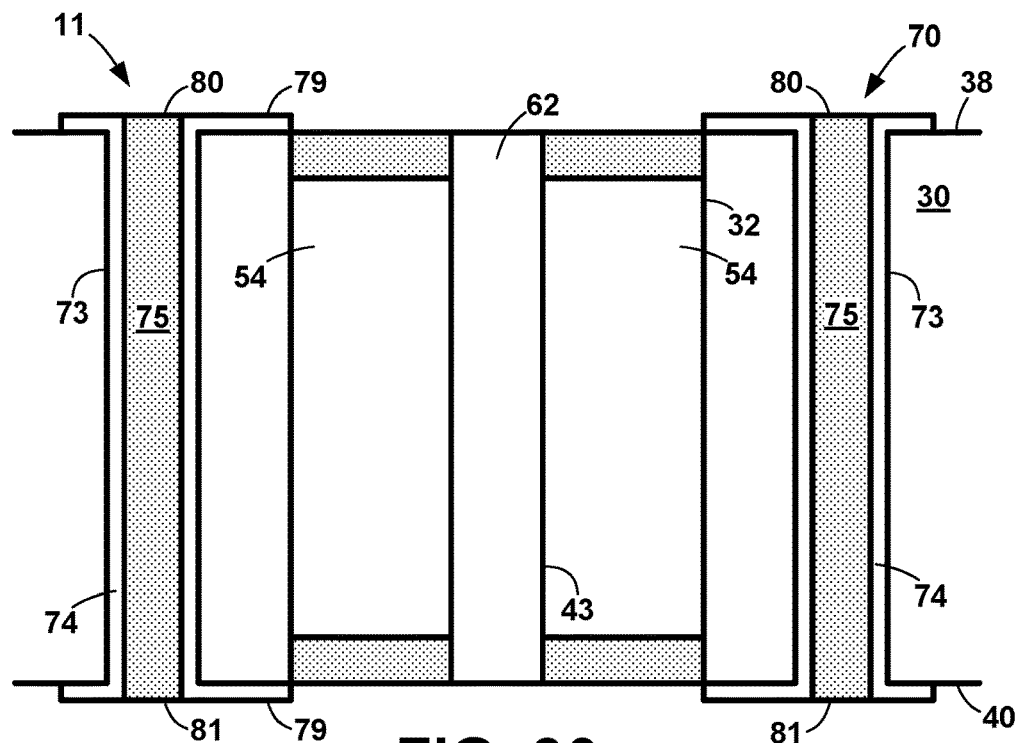
FIG. 30 is a cross-sectional view of a PCB block with ground links.
Figure 31:
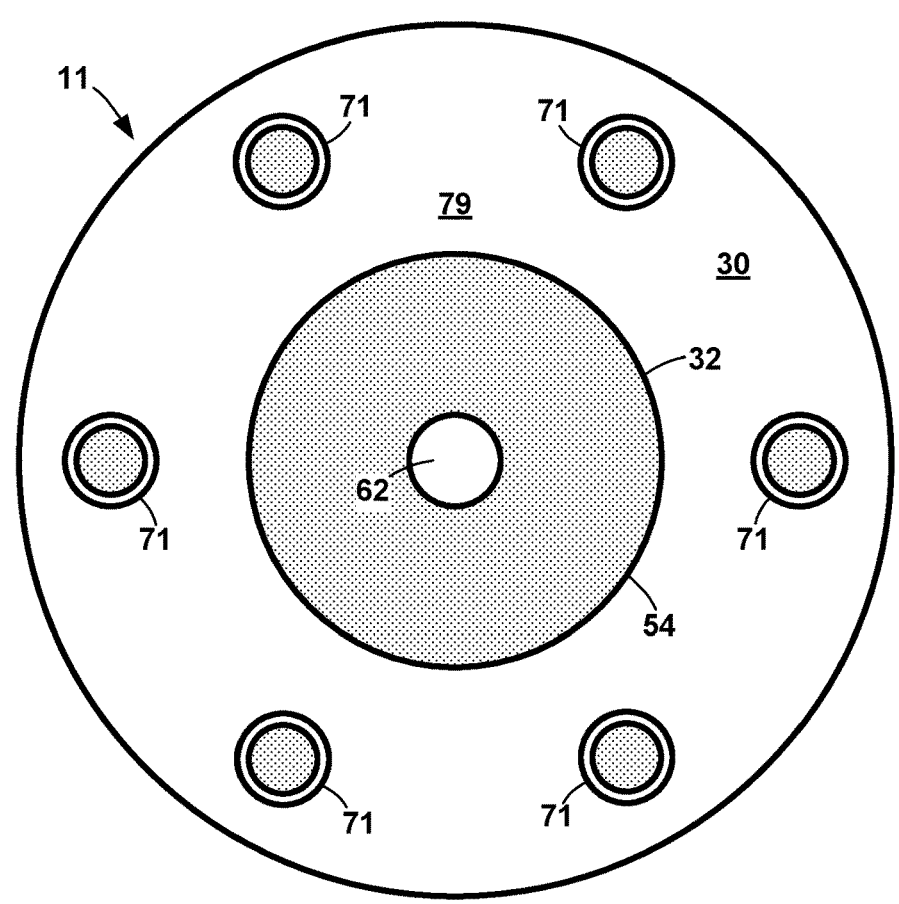
FIG. 31 is a top view of a feedthrough with ground links in a ground plane.

Optionally, the ground links 71 and ground apertures 72 are shaped to prevent the ground links 71 from being pushed through the ground apertures 72 during installation or if the first environment 1 is at a higher pressure than the second environment 2. The same geometries described above with reference to the signal link 62 can be used. For example, each ground link first end 80 has a head 78 that has a larger diameter than the rest of the ground link 71, as shown in FIG. 20.

Where the block 30 is of a PCB structure or composed of other dielectric material, the ground links 71 can be vias 73 through the block 30 that are plated, as at 74 in FIG. 30, to carry the ground signal through the block 30. The plated vias 73 surround the signal link 62 as described above and typically connect ground planes 79 on both surfaces 38, 40, as in FIGS. 30 and 31. The plated vias 73 are hermetically sealed by filling them with a potting material, such as an epoxy, as at 75, or solder.

The ground link ends 80, 81 are the contact points for the ground contacts 87 of the connectors 14, 16. In the case of vias 73, the plating 74 can be extended horizontally along the surface 38, 40 of the PCB to provide the contact points 80, 81 for the ground contacts 87.

Figure 32:
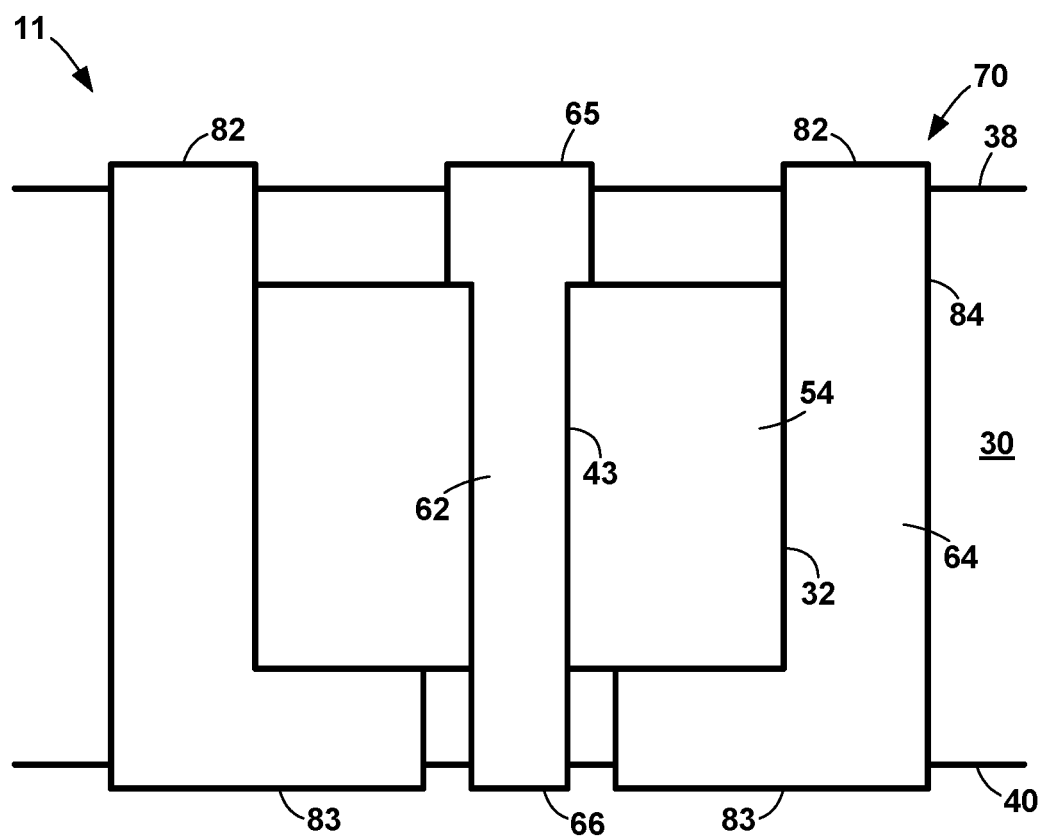
FIG. 32 is a cross-sectional view of a feedthrough with a ground ferrule.

In another configuration of the ground coupling 70, an electrically conductive ground ferrule 64 is installed in a ground ferrule through aperture 84 in the block 30 and the spacer 54 is installed in the spacer aperture 32 in the ground ferrule 64 such that the ground ferrule 64 surrounds the spacer 54, as in FIG. 32. The first end 82 of the ground ferrule and the first end 65 of the signal link 62 are flush and the second end 83 of the ground ferrule 64 and the second end 66 of the signal link 62 are flush. The term "flush" is intended to have the same meaning at described above, where the ferrule ends 82, 83, as be actually flush with, slightly recessed into, or slightly protruding from the associated block surface 38, 40.

The ferrule ends 82, 83 are the contact points for the ground contacts 87 of the connectors 14, 16. The ground ferrule 64 may be a different total height than the spacer 54 it is installed in. Preferably, the ferrule faces 82, 83 and signal link ends 65, 66 protrude from the corresponding block surface 38, 40, thereby ensuring good compression contact with the signal contact 86 and ground contacts 89.

In another configuration of the ground coupling 70, the wall 41 of the spacer aperture 32 is coated with a conductive material. For example, if the block 30 is a PCB, the spacer aperture 32 can be a plated via, as at 77 in FIG. 33, where the plating 77 is electrically connected to ground. The coating 77 can cover the entire wall 41 or can coat only part of the wall 41, for example, as stripes extending between the block surfaces 38, 40.

Figure 33:
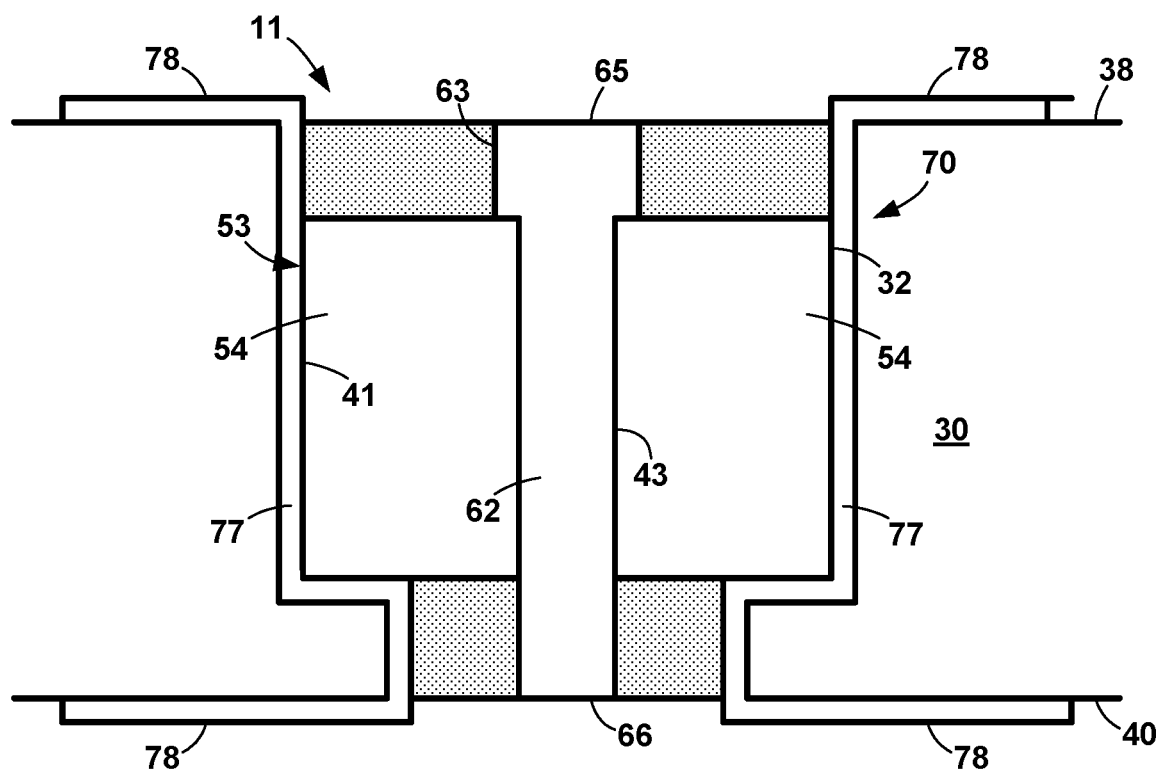
FIG. 33 is a cross-section of a feedthrough with a plated aperture and ground pads.

Optionally, the plating 77 in the spacer aperture 32, shown in FIG. 33, can be extended horizontally along the surface of the PCB to provide contact points 78 for the ground contacts 87 of the connectors 14, 16.

The signal link 62, ground coupling 70, and, when employed, the spacer 54 are installed with a hermetic seal to hermetically separate the two environments 1, 2. The hermetic seal can be formed in one or more of several different ways.

In the first, the various components are press fit into the corresponding apertures, leaving no gap between adjacent components. For example, with the insulating block 30, the signal link 62 is press fit into the signal aperture 43, leaving no gap between the signal link 62 and block 30. With the conductive block 30, the signal link 62 is press fit into the spacer signal aperture 43, leaving no gap between the signal link 62 and the spacer 54, and the spacer 54 is press fit into the spacer through aperture 32, leaving no gap between the spacer 54 and the block 30. Alternatively, the spacer 54 is molded around the signal link 62 and the spacer 54/signal link 62 combination is press fit into the spacer through aperture 32. Alternatively, the signal link 62 is held in the spacer through aperture 32 by a fixture and the spacer material is injected into the spacer through aperture 32 around the signal link 62 to form the spacer 54.

Optionally, the spacer 54 is composed of a slightly compressible material so that, when the spacer 54 is installed in the spacer aperture 32, the spacer 54 expands against the spacer aperture wall 41 and against the signal link 62 to form the hermetic seal.

Figure 24:
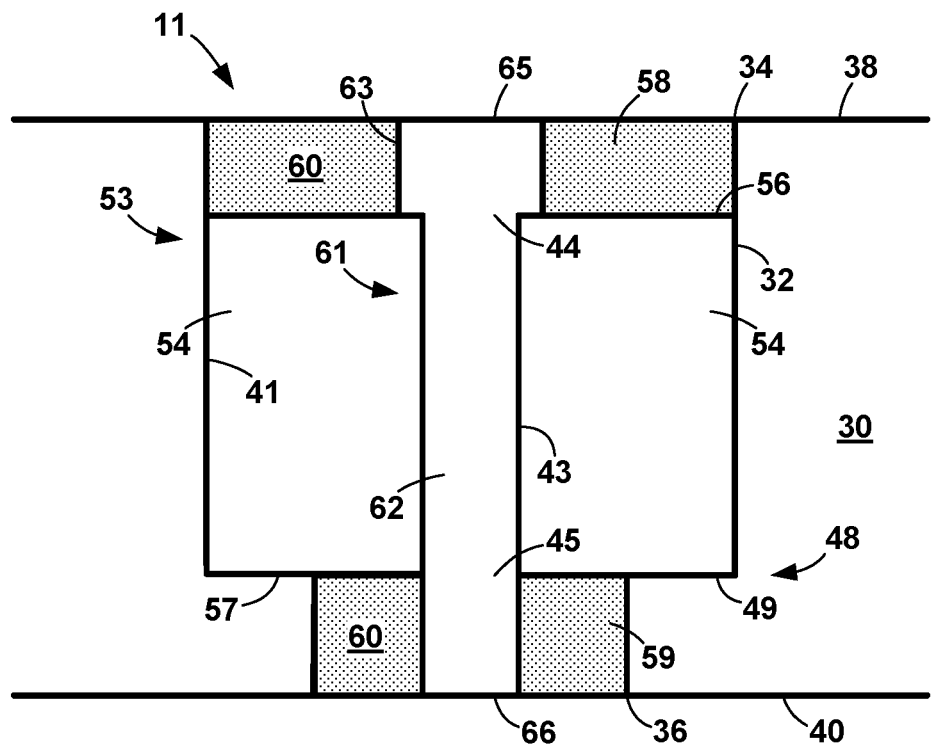
FIG. 24 is a cross-section of a feedthrough with alternate configurations of several components.
Figure 26:
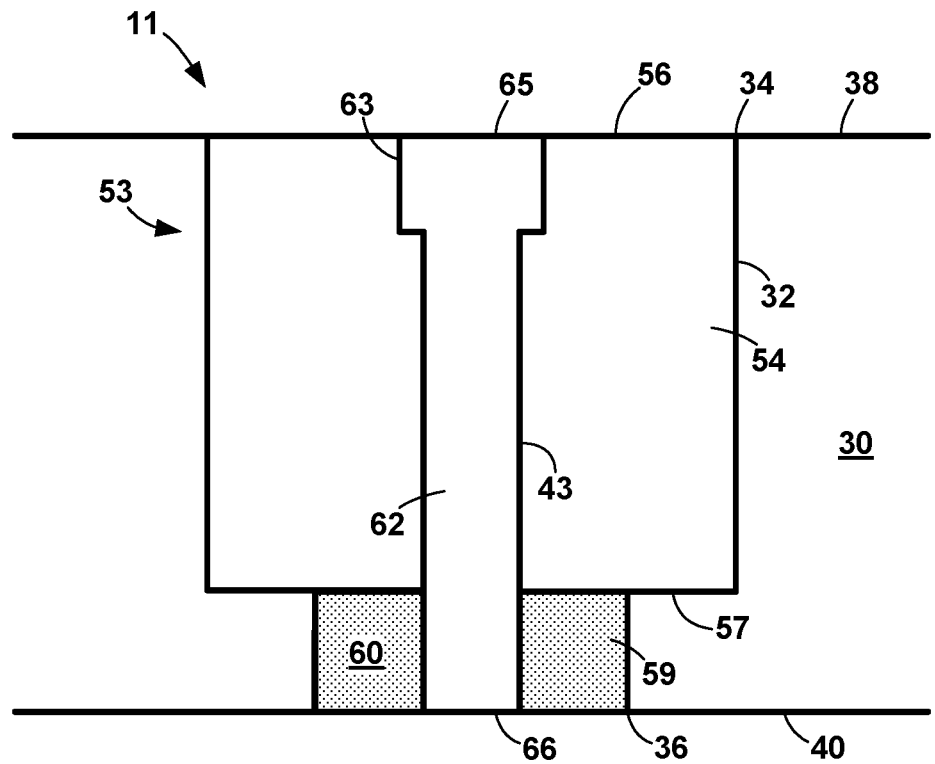
FIG. 26 is a cross-section of a feedthrough with alternate configurations of several components.
Figure 27:
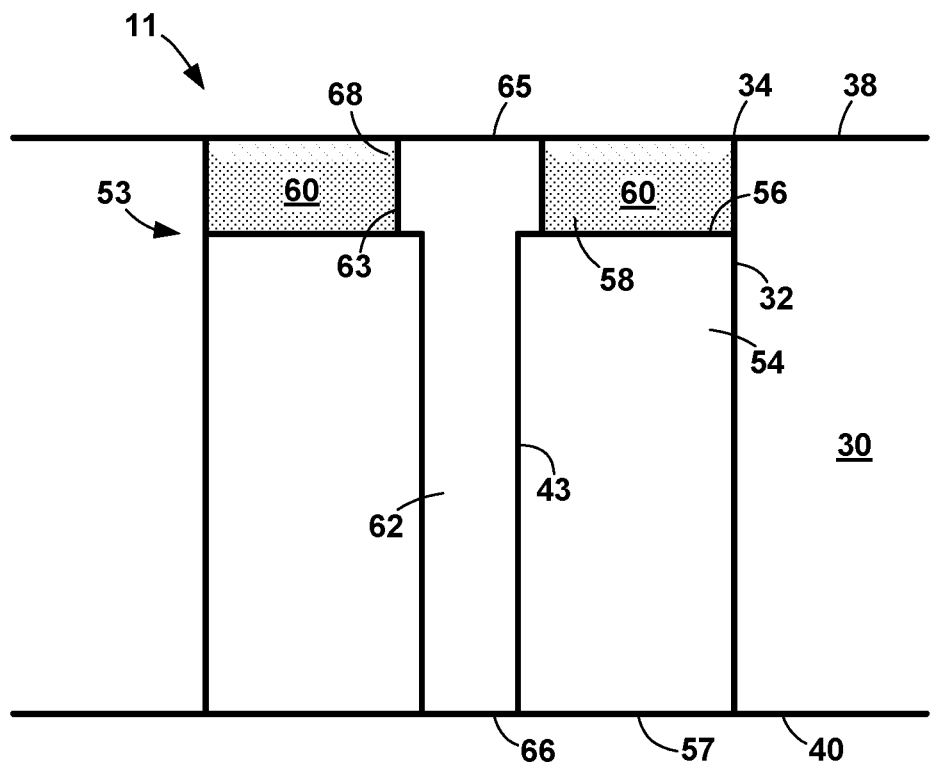
FIG. 27 is a cross-section of a feedthrough with alternate configurations of several components.

In the second method of providing a hermetic seal, shown in FIG. 24, the spacer 54 is shorter than the spacer aperture 32 so that both faces 56, 57 of the spacer 54 are recessed from the corresponding block surface 38, 40, thereby leaving a first gap 58 between the spacer first face 56 and the block first surface 38 and a second gap 59 between the spacer second face 57 and the block second surface 40. Alternatively, only one face 57 is recessed from the block surface 40, leaving only one gap 59, and the opposite spacer face 56 extends to the corresponding block surface 38, as in FIG. 26. Alternatively, only the other face 56 is recessed from the block surface 38, leaving only one gap 58, and the opposite spacer face 57 extends to the corresponding block surface 40, as in FIG. 27.

One or both of the gaps 58, 59 are potted, as at 60, to seal the spacer aperture 32 and around the signal link 62, thereby producing a hermetic seal. The typical potting material is a two-part epoxy, but any material that provides the desired seal and is minimally affected by the environment can be used. The minimum depth for each gap 58, 59 that will provide an adequate hermetic seal depends on the environment and the potting material. In one configuration, the gap depth is approximately 0.02 inch and not less than 0.01 inch.

Most of the figures show that the potting material 60 is flush with the block surfaces 38, 40, although this is not required. The potting material 60 can be recessed in the gaps 58, 59, as in FIG. 27. Because the potting material 60 is initially liquid, it may form a meniscus 68 on its surface.

Plated vias 73 are hermetically sealed by filling them with the potting material, as at 75 in FIG. 30, or solder.

One method of potting involves applying a vacuum to one surface 40 of the block 30 and allowing the vacuum to pull the potting material 60 from the opposite side, thereby forcing the potting material 60 into the gap 58 and all of the interfaces between components, such as between the signal link 62 and the spacer 54 or block 30, between the spacer 54 and block 30, and between each ground link 71 and block 30. The vacuum assures that the potting material 60 is forced into all of the spaces that would provide a leak path between the two environments 1, 2. Of course, the vacuum can be applied in the opposite direction, from the other surface 38.

In another method of potting, pressure is applied to the potting material at one surface 38, 40 to push the potting material 60 into all of the spaces that would provide a leak path between the two environments 1, 2.

The press fit and potting methods can be employed simultaneously. For example, the shorter spacer 54 of FIG. 24 is sized to be press fit into the aperture 32 and the signal link 62 is press fit into the signal aperture 43, and then the gaps 58, 59 are potted.

Figure 34:
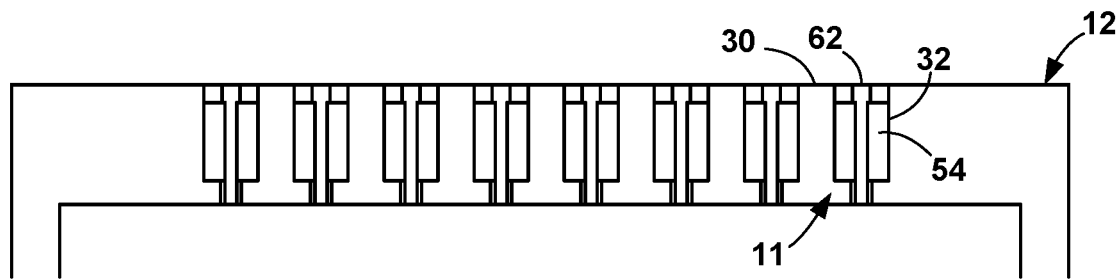
FIG. 34 is a cross-section of the block as part of the flange.
Figure 35:
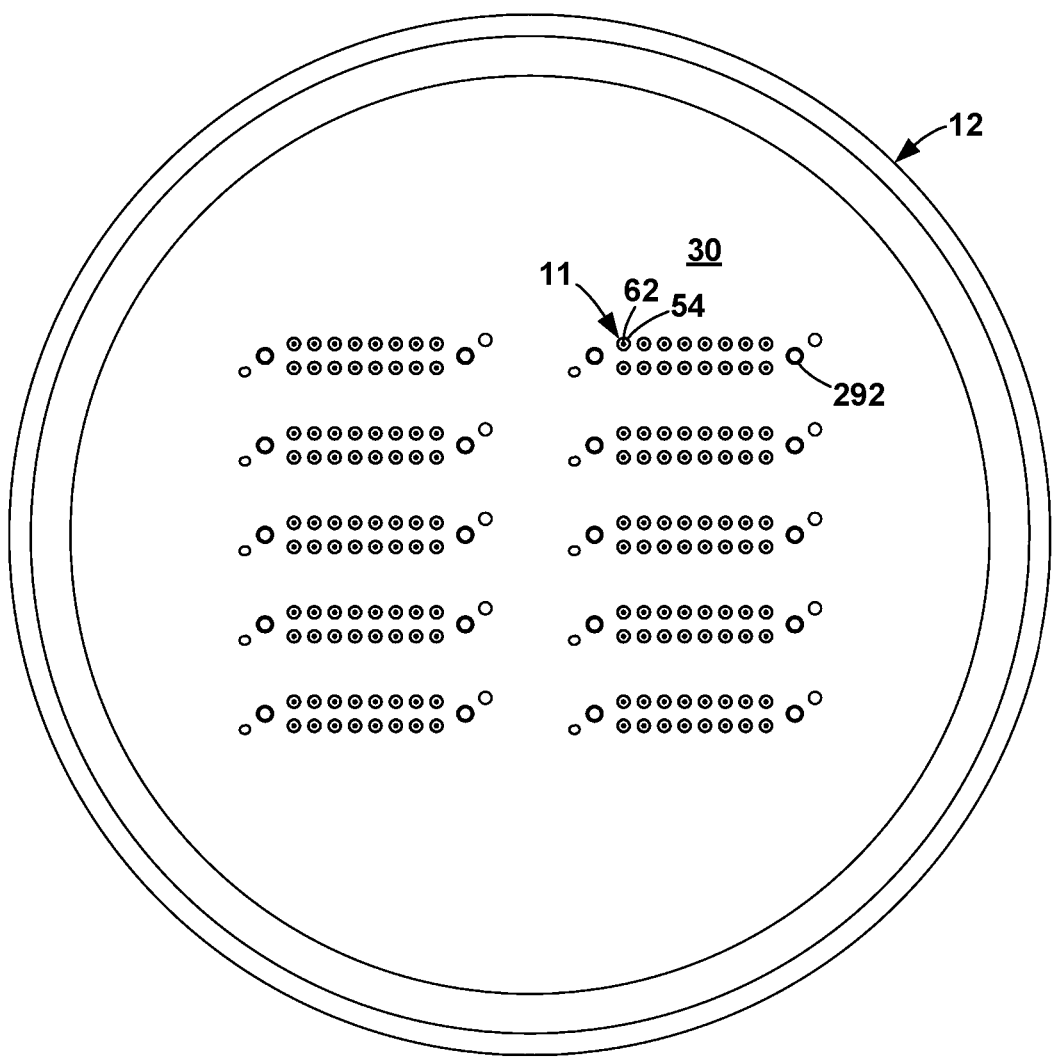
FIG. 35 is a top view of a flange as the block.

The present invention contemplates that the flange 12 is the block 30, that is, the feedthroughs 11 extend through the flange 12 itself, as in FIGS. 34 and 35.

Figure 36:
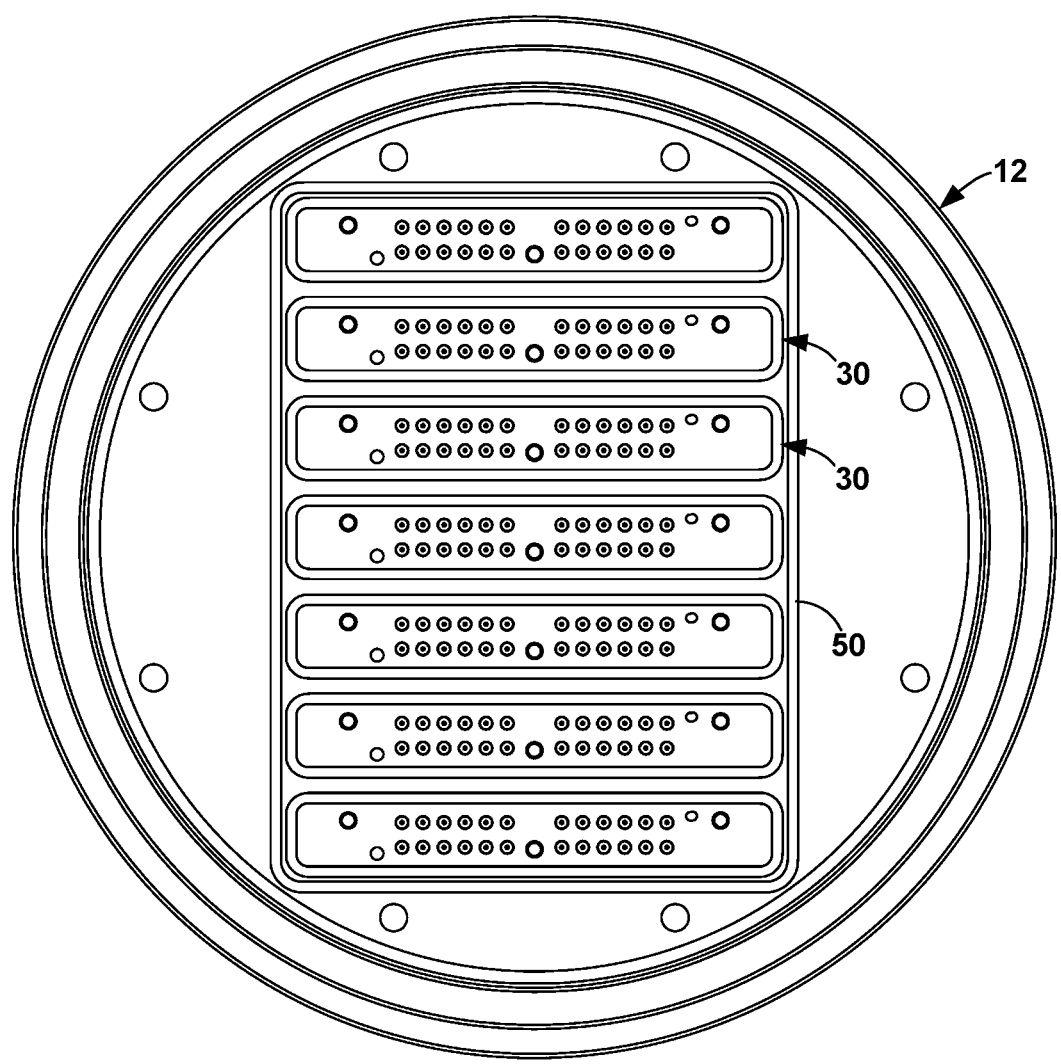
FIG. 36 is a top view of a flange with independent blocks.
Figure 37:
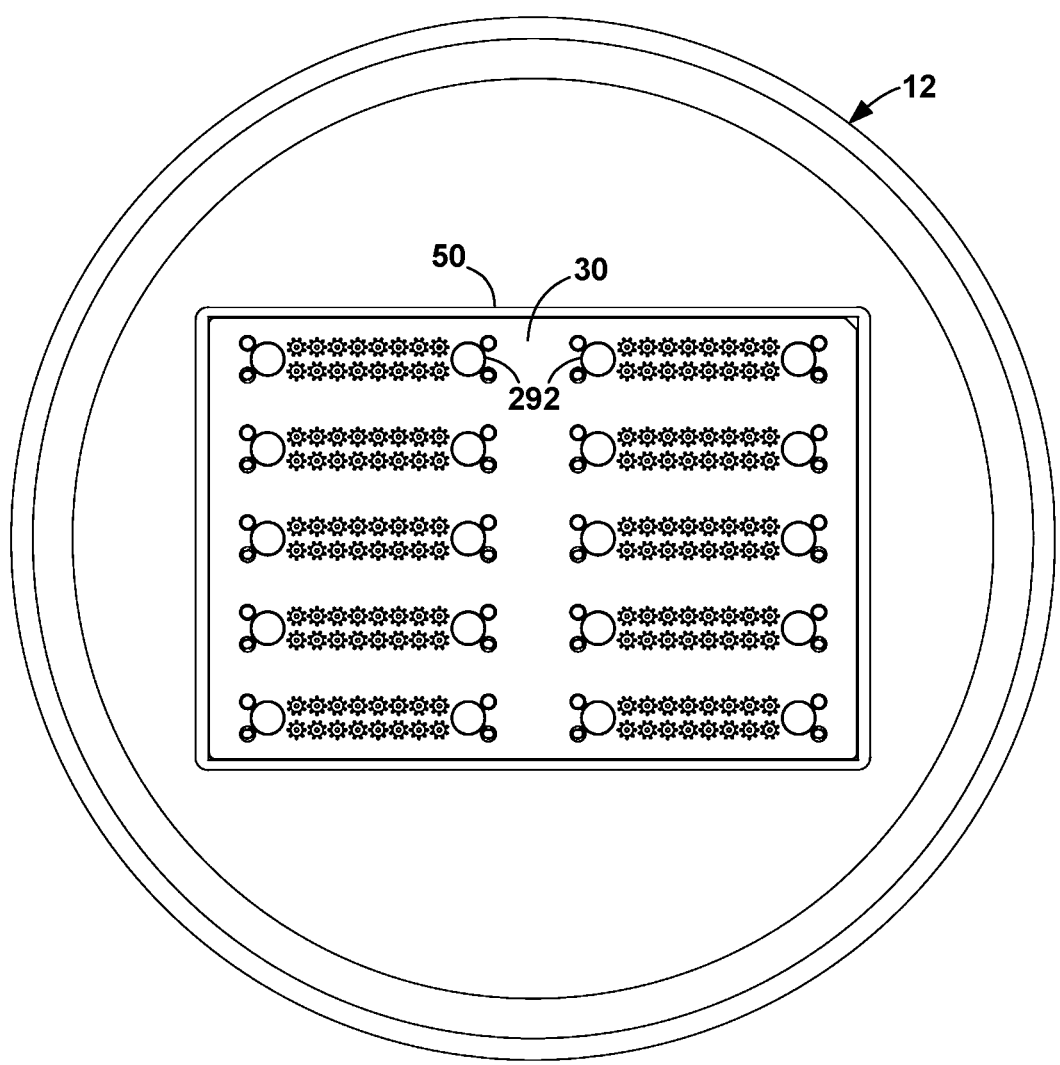
FIG. 37 is a top view of the flange with a PCB as the block.

Alternatively, the block 30 is an independent component that is hermetically sealed into an opening 50 in the flange 12. The block 30 can be similar to a connector body or the block 30 can be a printed circuit board. With the former, there may be more than one block 30 mounted in the flange 12, as in FIG. 36. With the later, typically, a single PCB is mounted into the flange 12, as in FIG. 37, although more than one PCB can be used, as in FIG. 36. The block 30 is mounted into the opening 50 by whatever means is appropriate, such as by screws or other mechanical means. The seam between the block 30 and flange 12 can be potted to provide a hermetic seal. Alternatively, a gasket can be used to provide the hermetic seal.

Figure 38:
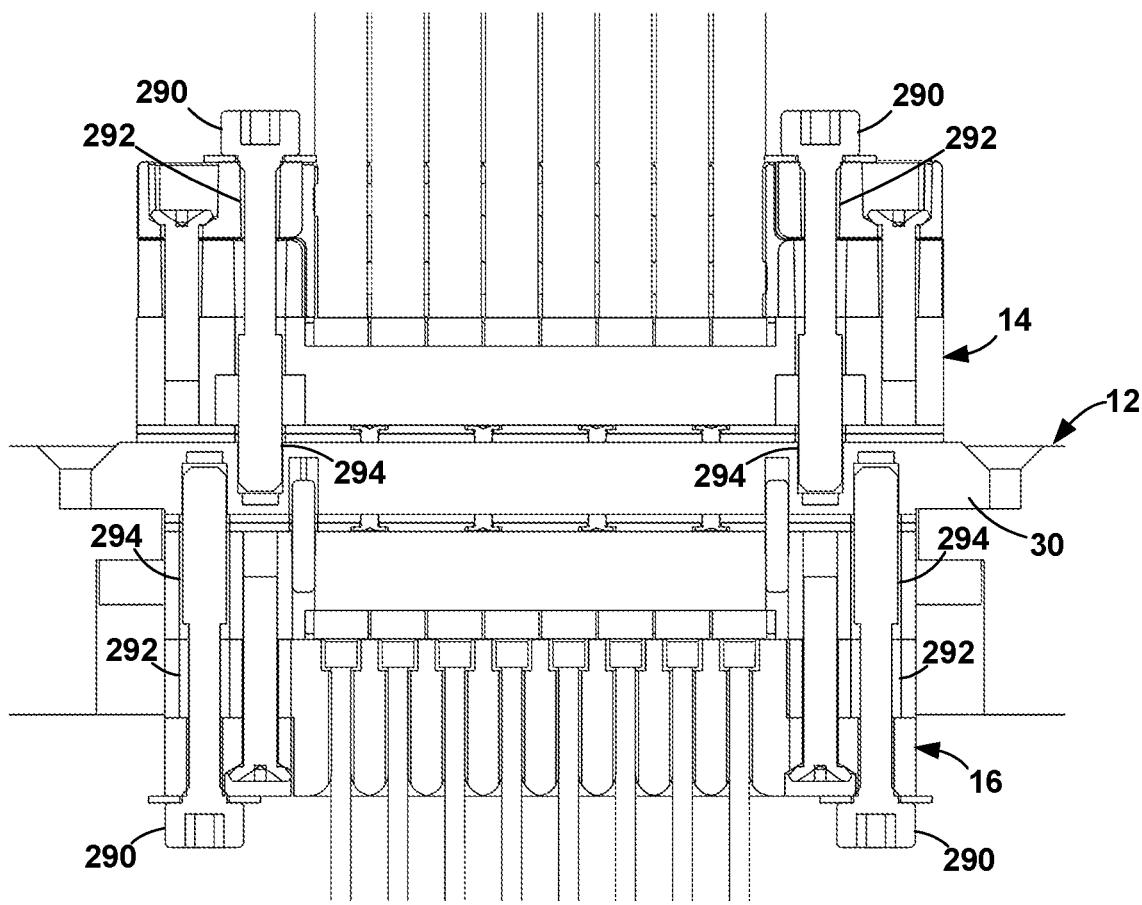
FIG. 38 is a cross-sectional view showing connection of the connectors to the feedthrough block.

The connectors 14, 16 removably connect to the feedthrough block 30. The typical connection mechanism is via jackscrews 290, shown in FIG. 38. The jackscrews 290 extend through holes 292 in the anchor block 88 and turn into threaded holes 294 in the feedthrough block 30.

Figure 39:
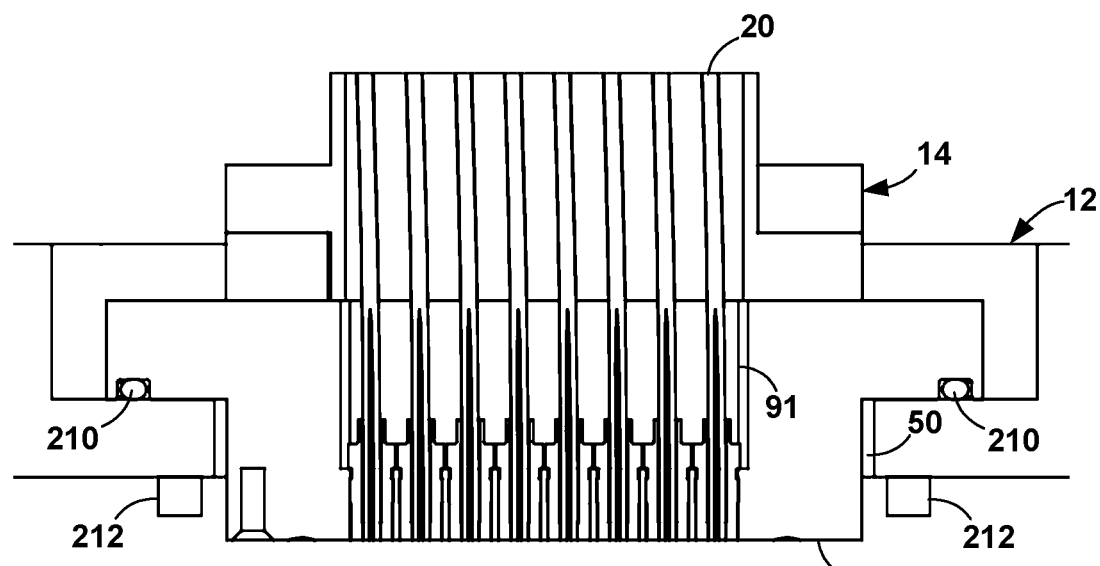
FIG. 39 is a cross-sectional view of another embodiment.
Figure 40:
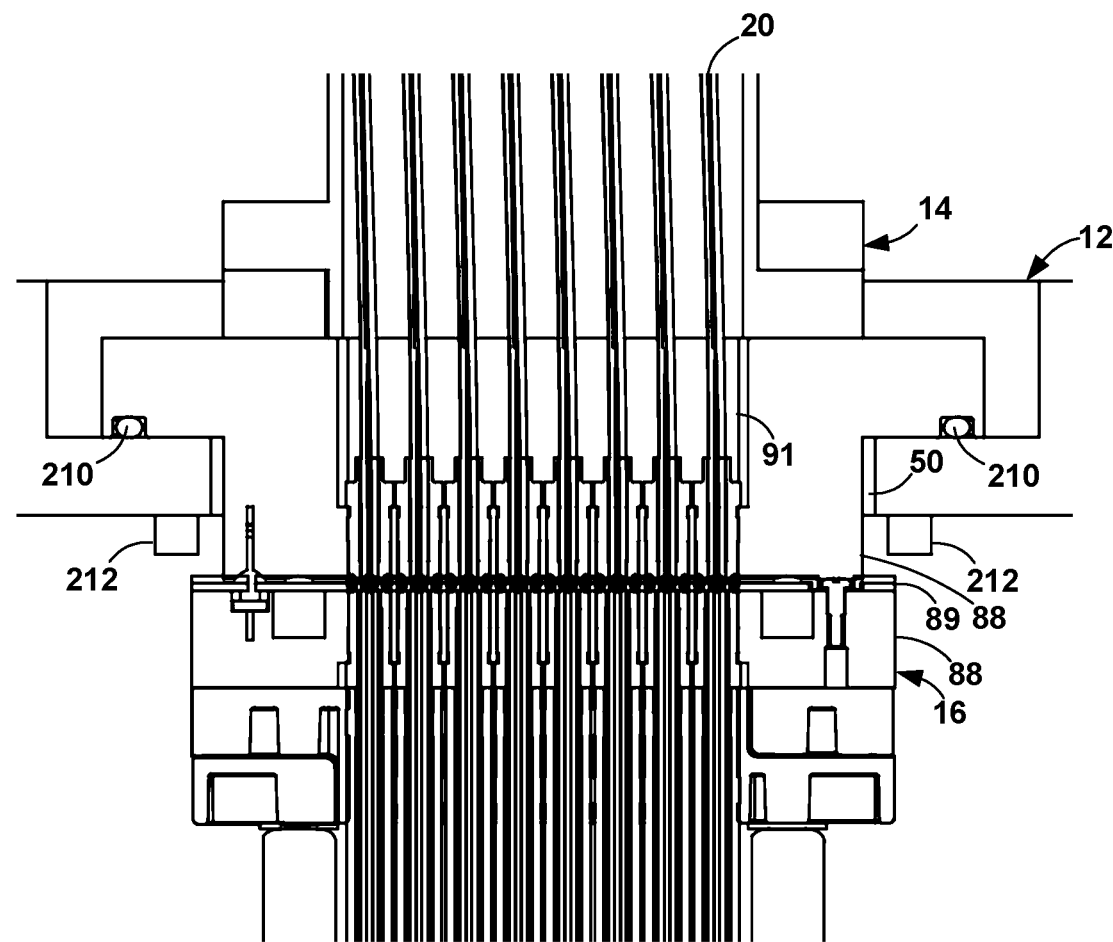
FIG. 40 is a cross-sectional view of the embodiment of FIG. 39 with a connector attached.
Figure 41:
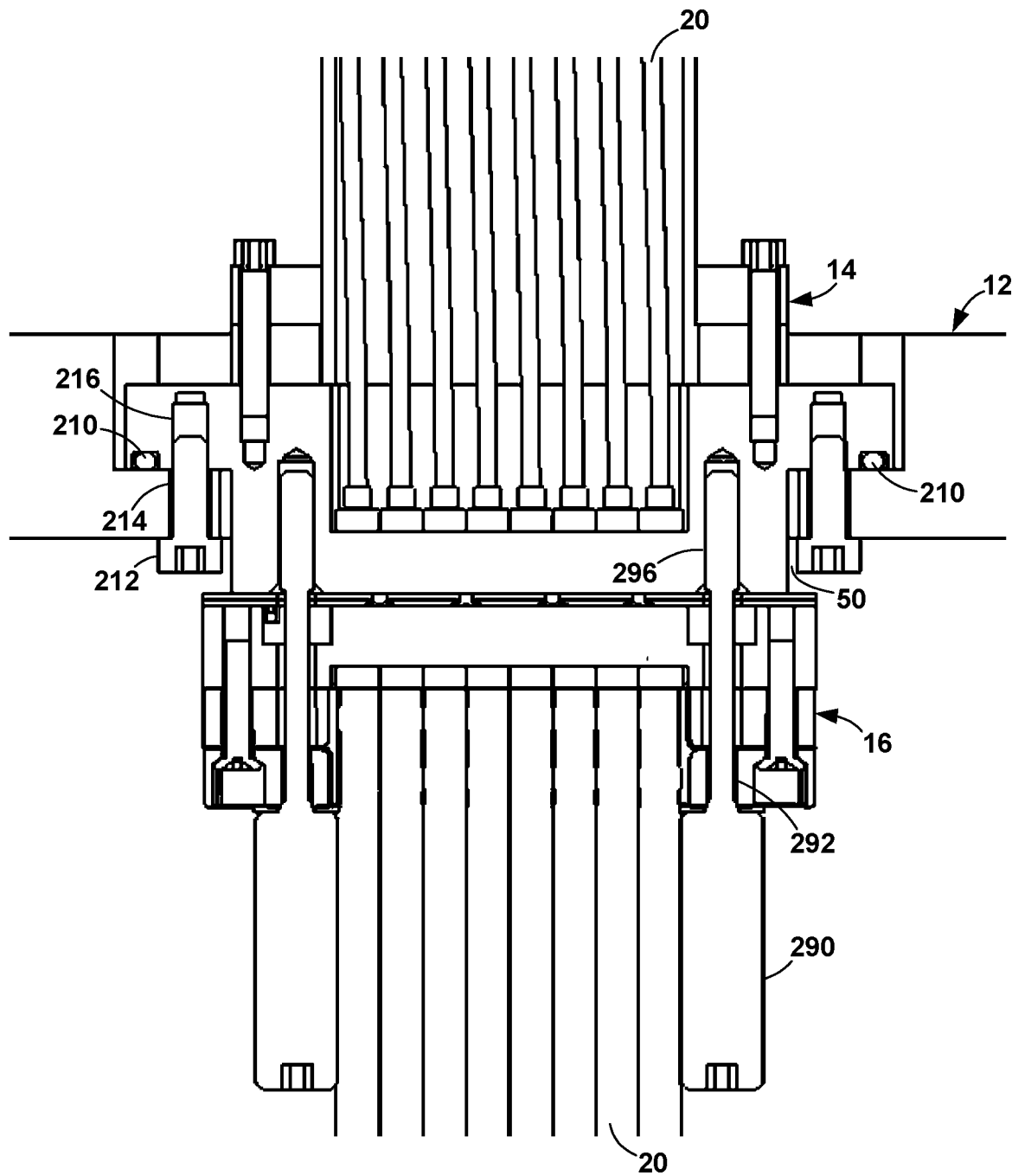
FIG. 41 is another cross-sectional view of the embodiment of FIG. 39 with a connector attached.

Another embodiment is shown in FIGS. 39-41. The feedthrough block 30 is the anchor block 88 of a connector 14. The anchor block 88 is mounted to the opening 50 in the flange 12 with an O-ring 210 to provide the hermetic seal. Preferably, the connector 14 is mounted to be removable from the flange 12. Jackscrews 212 extend through holes 214 in the flange 12 and turn into threaded holes in the anchor block 88.

The cable holes 91 of the anchor block 88 are also hermetically sealed. If the cable 20 is permanently attached, the attachment means (soldering, crimping, potting with a conductive adhesive, insert molding) provides the hermetic seal. If the cable 20 is removably attached in the cable holes 91, the cable holes 91 are potted to hermetically seal them after the cable 20 is installed.

The connectors 14, 16 removably connect to each other with a single plate 89 that is attached to the removable connector 16. The typical connection mechanism is via jackscrews 290. The jackscrews 290 extend through holes 292 in the anchor block 88 of the removable connector 16 and turn into threaded holes 296 in the anchor block 88 of the connector 14 mounted to the flange 12, as in FIG. 41.

The present invention contemplates signals much closer together than can be had with SMAs or SMPs, thereby increasing the total channel density greatly. Signal spacing can be 0.1 inch or smaller, making density of channels more than double the current state of the art.

Material and construction are picked for mechanical integrity due to environmental pressures and cycle life, minimizing the leak rate as much as possible, ensuring the intended controlled impedance, and minimal out gassing. The thickness of the block 30 is driven by the mechanical strength of the block material. In the case of one environment being at a different pressure than the other environment, the block 30 must be thick enough to stay relatively flat, for example, +/−0.01 inch over the area of the surfaces 38, 40 in order to insure a proper mating face. Otherwise, the thickness of the block 30 is not critical.

Thus, it has been shown and described a hermetically sealed controlled impedance feedthrough assembly. Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. A controlled impedance feedthrough assembly between a first environment and a second environment, the feedthrough assembly comprising:
    (a) an electrically conductive block having a first surface and a second surface;
    (b) at least one feedthrough in the block extending between the first surface and the second surface, the feedthrough comprising:
        (1) a spacer through aperture extending between the first surface and the second surface;
        (2) a dielectric spacer within the spacer through aperture having a first face and a second face;
        (3) a signal through aperture extending between the first face and the second face; and
        (4) a rigid, electrically-conductive signal link in the signal through aperture having a first end at the first surface and a second end at the second surface;
    (c) the feedthrough being hermetically sealed by one of either the first face being recessed from the first surface forming a first gap that is filled with a potting material or the second face being recessed from the second surface forming a second gap that is filled with the potting material.

2. The controlled impedance feedthrough assembly of claim 1 wherein the first gap or the second gap is at least 0.01 inch in depth.

3. The controlled impedance feedthrough assembly of claim 1 wherein the potting material is an epoxy.

4. The controlled impedance feedthrough assembly of claim 1 further comprising a flange separating the first environment and the second environment, the block being mounted within an opening in the flange, the seam between the block and flange being hermetically sealed.

5. The controlled impedance feedthrough assembly of claim 1 wherein the signal link and signal through aperture are shaped to prevent the signal link from being pushed through the signal through aperture and wherein the spacer and spacer aperture are shaped to prevent the spacer from being pushed through the spacer aperture.

6. The controlled impedance feedthrough assembly of claim 5 wherein the first end of the signal link has a head with a larger diameter than a diameter of the signal through aperture.

7. The controlled impedance feedthrough assembly of claim 5 wherein the spacer aperture has a stepped diameter creating a shoulder such that a diameter of the first opening is larger than the diameter of the second opening, and wherein the spacer abuts the shoulder.

8. A controlled impedance feedthrough assembly between a first environment and a second environment, the feedthrough assembly comprising:
    (a) an electrically conductive block having a first surface and a second surface;
    (b) at least one feedthrough in the block extending between the first surface and the second surface, the feedthrough comprising:
        (1) a spacer through aperture extending between the first surface and the second surface;
        (2) a dielectric spacer within the spacer through aperture having a first face and a second face;
        (3) a signal through aperture extending between the first face and the second face; and
        (4) a rigid, electrically-conductive signal link in the signal through aperture having a first end at the first surface and a second end at the second surface;
    (c) the feedthrough being hermetically sealed by at least one of the first face being recessed from the first surface forming a first gap and the second face being recessed from the second surface forming a second gap, and at least one of the first gap and second gap being filled with a potting material.

9. The controlled impedance feedthrough assembly of claim 8 wherein the first gap or the second gap is at least 0.01 inch in depth.

10. The controlled impedance feedthrough assembly of claim 8 wherein the potting material is an epoxy.

11. The controlled impedance feedthrough assembly of claim 8 further comprising a flange separating the first environment and the second environment, the block being mounted within an opening in the flange, the seam between the block and flange being hermetically sealed.

12. The controlled impedance feedthrough assembly of claim 8 wherein the signal link and signal through aperture are shaped to prevent the signal link from being pushed through the signal through aperture and wherein the spacer and spacer aperture are shaped to prevent the spacer from being pushed through the spacer aperture.

13. The controlled impedance feedthrough assembly of claim 12 wherein the first end of the signal link has a head with a larger diameter than a diameter of the signal through aperture.

14. The controlled impedance feedthrough assembly of claim 12 wherein the spacer aperture has a stepped diameter creating a shoulder such that a diameter of the first opening is larger than the diameter of the second opening, and wherein the spacer abuts the shoulder.

\* \* \* \* \*